(12) United States Patent
Bolin et al.

(10) Patent No.: US 8,211,914 B2
(45) Date of Patent: Jul. 3, 2012

(54) INHIBITORS OF DIACYLGLYCEROL ACYLTRANSFERASE

(75) Inventors: David Robert Bolin, Montclair, NJ (US); Adrian Wai-Hing Cheung, Glen Rock, NJ (US); Fariborz Firooznia, Florham Park, NJ (US); Nicholas Marcopulos, North Caldwell, NJ (US); Yimin Qian, Wayne, NJ (US)

(73) Assignee: Madrigal Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/638,244

(22) Filed: Dec. 15, 2009

(65) Prior Publication Data

US 2010/0152445 A1 Jun. 17, 2010

Related U.S. Application Data

(60) Provisional application No. 61/138,157, filed on Dec. 17, 2008.

(51) Int. Cl.
*A61K 31/445* (2006.01)
*C07D 413/12* (2006.01)

(52) U.S. Cl. ........ 514/326; 546/184; 546/192; 546/209; 514/315

(58) Field of Classification Search ................ 546/184, 546/192, 209; 514/315, 326
See application file for complete search history.

(56) References Cited

U.S. PATENT DOCUMENTS

| | | | |
|---|---|---|---|
| 3,250,771 A | 5/1966 | Leonard et al. | |
| 3,929,793 A | 12/1975 | Popelak et al. | |
| 4,066,654 A | 1/1978 | Adelstein et al. | |
| 7,015,218 B1 | 3/2006 | Ushio et al. | |
| 7,094,896 B2 | 8/2006 | Ding et al. | |
| 7,148,246 B2 | 12/2006 | Gretzke et al. | |
| 7,160,911 B2 | 1/2007 | Goerlitzer et al. | |
| 7,244,727 B2 | 7/2007 | Fox et al. | |
| 7,317,125 B2 | 1/2008 | Bolin et al. | |
| 7,714,126 B2 * | 5/2010 | Bolin et al. | 544/59 |
| 2004/0019067 A1 | 1/2004 | Armistead et al. | |
| 2007/0123504 A1 | 5/2007 | Bolin et al. | |
| 2009/0093497 A1 | 4/2009 | Bolin et al. | |
| 2009/0099201 A1 | 4/2009 | Bolin et al. | |
| 2009/0105273 A1 | 4/2009 | Bolin et al. | |
| 2009/0170864 A1 | 7/2009 | Bolin et al. | |
| 2010/0035864 A1 | 2/2010 | Bolin et al. | |
| 2010/0145047 A1 | 6/2010 | Bolin et al. | |

FOREIGN PATENT DOCUMENTS

| | | |
|---|---|---|
| AU | 2002333456 A2 | 3/2003 |
| EP | 1535915 A | 6/2005 |
| EP | 1535915 A1 | 6/2005 |
| WO | WO-0047558 A1 | 8/2000 |
| WO | 03020269 A | 3/2003 |
| WO | 2006134317 A | 12/2006 |
| WO | 2007/060140 A | 5/2007 |
| WO | 2008141976 A1 | 11/2008 |
| WO | WO-2010017040 A1 | 2/2010 |
| WO | WO-2010065310 A1 | 6/2010 |
| WO | WO-2010077861 A1 | 7/2010 |

OTHER PUBLICATIONS

The International Search Report and Written Opinion by the International Searching Authority, issued on Jul. 30, 2008, in the PCT application No. PCT/EP2008/055843.
The International Search Report and Written Opinion by the International Searching Authority, issued on Mar. 2, 2010, in the PCT application No. PCT/US09/68048.
The restriction requirement for U.S. Appl. No. 12/113,295, issued on Mar. 3, 2010.
The restriction requirement for U.S. Appl. No. 12/113,275, issued on Mar. 10, 2010.
Mishra et al., "A molecular model for diacylglycerol acyltransferase from Mortierella ramanniana var. angulispora," Bioinformation. 2009; 3(9): 394-398.
Oh et al., "Diacylglycerol acyltransferase-inhibitory compounds from Erythrina senegalensis," Archives of Pharmacal Research, 32(1), pp. 43-47, Jan. 2009.
Birch et al., "Discovery of a potent, selective, and orally efficacious pyrimidinooxazinyl bicyclooctaneacetic acid diacylglycerol acyltransferase-1 inhibitor," J. Med Chem. Mar. 26, 2009;52(6):1558-68.
Zhao et al., "Validation of Diacyl Glycerolacyltransferase I as a Novel Target for the Treatment of Obesity and Dyslipidemia Using a Potent and Selective Small Molecule Inhibitor," J. Med. Chem., 2008, 51 (3), pp. 380-383.
Burger, A., "Isosterism and Bioisosterism in Drug Desing," Progress in Drug Research, 1991, pp. 287-328.
Patani, G. and LaVoie, E., "Bioisosterism: A Rational Approach in Drug Design," Chem. Rev. 1996, 96, 3147-3176.
The International Search Report and Written Opinion by the International Searching Authority, issued on Apr. 2, 2010, in the PCT application No. PCT/US09/64971.

* cited by examiner

*Primary Examiner* — Golam M M Shameem
(74) *Attorney, Agent, or Firm* — Mintz Levin Cohn Ferris Glovsky and Popeo, P.C.; Ivor R. Elrifi; Heidi A. Erlacher

(57) ABSTRACT

Provided herein are amides containing at least a four ring structure, which are inhibitors of diacylglycerol acyltransferase and are useful for the treatment of diseases such as, for example, obesity, type II diabetes mellitus and metabolic syndrome.

55 Claims, No Drawings

INHIBITORS OF DIACYLGLYCEROL ACYLTRANSFERASE

RELATED APPLICATIONS

This application is related to U.S. Provisional Application No. 61/138,157 filed on Dec. 17, 2008, the priority of which is claimed for this application.

FIELD OF THE INVENTION

The invention involves inhibitors of diacylglycerol acyltransferase. The inhibitors are useful for the treatment of diseases such as obesity, type II diabetes mellitus, dyslipidemia and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT have been cloned and are designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is low homology between DGAT1 and DGAT2. Both enzymes are widely expressed, however some differences do exist in the relative abundance of expression in various tissues.

The gene encoding mouse DGAT1 has been used to create DGAT knock-out. These mice, although unable to express a functional DGAT enzyme (Dgat−/− mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat−/− mice are resistant to diet-induced obesity and remain lean. When fed a high fat diet, Dgat−/− mice maintain weights comparable to mice fed a diet with regular fat content. Dgat−/− mice have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat−/− mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 1.88-192).

Disorders or imbalances in triglyceride metabolism, both absorption as well as de novo synthesis, have been implicated in the pathogenesis of a variety of disease risks. These include obesity, insulin resistance syndrome, type II diabetes, dyslipidemia, metabolic syndrome (syndrome X) and coronary heart disease (see Kahn, Nature Genetics (2000) 25, 6-7, Yanovski and Yanovski, New England. Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets—Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1.996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), substituted sulfonamides (see Budd Haeberlein and Buckett, WO20050442500), thiophenoxyacetamides (see Bolin and Michoud, WO2006082010), arylpropionylhydrazides (see Michoud, WO2006120125) and oxazoledicarboxamides (see Bolin et al, WO2007060140). Most recently, DGAT inhibitors demonstrated efficacy of body weight gain inhibition in obese animal models (Journal of Medicinal Chemistry (2008), 51, 380).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133). Also known to be modulators of DGAT activity are antisense oligonucleotides (see Monia and Graham, US20040185559).

A need exists in the art, however, for additional DGAT inhibitors that have efficacy for the treatment of metabolic disorders such as, for example, obesity, type II diabetes mellitus and metabolic syndrome.

SUMMARY OF THE INVENTION

The present invention pertains to DGAT inhibitors. In a preferred embodiment, the invention provides for compounds of the formula (I):

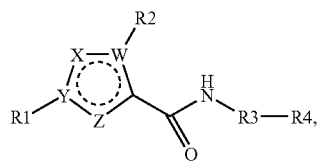

(I)

as well as pharmaceutically acceptable salts thereof, and pharmaceutical compositions thereof.

DETAILED DESCRIPTION OF THE INVENTION

In a preferred embodiment of the present invention, provided are compounds of formula (I):
wherein:

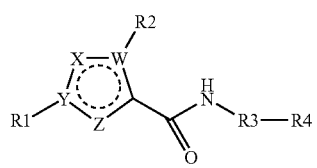

(I)

X is C, O or N;
Y is C or N;
Z is C or N;
W is C or S, wherein if W is S, then R2 is absent;

R1 is unsubstituted heteroaryl, unsubstituted aryl, or aryl substituted with —OCF3;
R2 is H, lower alkyl or haloloweralkyl;
R3 is phenyl, pyridine or pyrimidine; and
R4 is -piperidine-trifluoromethylphenyl,
-piperazine-1-yl-benzoic acid lower alkyl ester,
-piperazine-pyrimidine,
-piperazine-lower alkoxy phenyl,
-piperazine-trifluoromethylphenyl,
-hydroxy-piperidine-lower alkoxy phenyl,
-piperazine-phenyl,
-hydroxy-piperidine-phenyl,
-piperidine-phenyl,
-hydroxy piperidine-trifluoromethylphenyl,
-piperidine-trifluoromethylphenyl,
-piperazine-halophenyl,
-piperazine-benzoic acid,
-piperidine-lower alkyl oxadiazole,
-piperidine-cycloloweralkyloxadiazole,
-pyrrolidine-lower alkyl oxadiazole,
-piperidine-pyridinecarboxylic acid,
—O-pyrrolidine-benzoic acid
—O-pyrrolidine-benzoic acid lower alkyl esters
-pyrrolidine-benzoic acid lower alkyl esters
-pyrrolidine-benzoic acid,
-piperidine-benzoic acid or
-piperidine-benzoic acid lower alkyl ester
or a pharmaceutically acceptable salt thereof.

in another preferred embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

Among the preferred compounds of formula I are included the following compounds:
Compounds of the formula

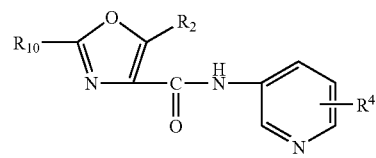

I-A wherein $R_{10}$ is heteroaryl, phenyl, or phenyl substituted with —OCF$_3$, and $R_2$; and $R^4$ are as above;
or its pharmaceutically acceptable salts;
Compounds of the formula

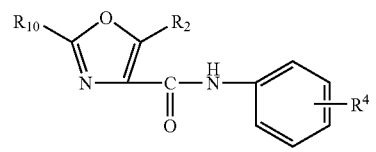

I-B wherein $R_{10}$ is heteroaryl, phenyl, or phenyl substituted with —$OCF_3$; and $R_2$, $R_{10}$ and $R^4$ are as above;
or its pharmaceutically acceptable salts;
Compounds of the formula

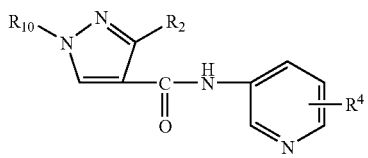

I-C wherein $R_{10}$ is heteroaryl, phenyl or phenyl substituted with —$OCF_3$; and $R_2$ and $R^4$ are as above
or its pharmaceutically acceptable salts; and
Compounds of the formula

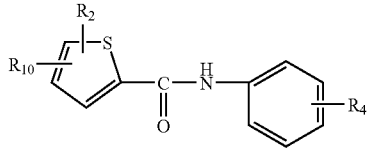

I-D wherein $R_{10}$ is heteroaryl, phenyl or phenyl substituted with an —$OCF_3$; $R^2$ and $R_4$ are as above;
or its pharmaceutically acceptable salts.

In the compounds of formula I-A, I-B, I-C, and I-D where $R_{10}$ is a heteroaryl radical, the preferred heteroaryl radical is a heteroaryl radical with a single 5 or 6 membered ring, most preferably unsubstituted, with from 1 to 2 hetero atoms selected from the group consisting of N, O or S.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. The preferred cycloalkyl group is cyclolower-alkyl which is a monovalent monocarbocyclic radical of three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can unsubstituted or optionally substituted with one, two, three or four substituents, with the understanding that said substituents are not, in turn, substituted further unless indicated otherwise. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, azetidine, morpholinyl, thiomorpholinyl, piperazinyl, piperidinyl, pyrrolidinyl, tetrahydropyranyl, tetrahydrofuranyl, 1,3-dioxanyl, thiazolidine-2,4-dione and the like. The heterocycloalkyl groups may be unsubstituted or substituted and attachment may be through their carbon frame or through their heteroatom(s) where appropriate, with the understanding that said substituents are not, in turn, substituted further.

The term "lower alkyl", alone or in combination with other groups, refers to a branched or straight-chain alkyl radical of one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like. The preferred aryl radical is phenyl or phenyl substituted with triflouromethyl.

The alkyl, loweralkyl and aryl groups may be substituted or unsubstituted. When substituted, there will generally be, for example, 1 to 4 substituents present, with the understanding that said substituents are not, in turn, substituted further unless indicated otherwise. These substituents may optionally form a ring with the alkyl, loweralkyl or aryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, aryl sulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidinyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. The preferred hetroaryl group is a heteroaryl radical containing one 5 or 6 membered hertroaryl ring with 1 or 2 one hetroatoms selected from the group consisting of nitrogen, oxygen and sulphur with the remainder of the ring being carbon.

The heteroaryl group described above may be unsubstituted or substituted independently with one, two, or three substituents, with the understanding that said substituents are not, in turn, substituted further unless indicated otherwise. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl) alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl, carbamates (e.g. alkoxycarbonylamino, aryloxycarbonylamino, aminocarbonyloxy, mono- or id-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfonylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless indicated otherwise. The preferred alkoxy group is a lower alkoxy group containing from 1 to 6 carbon atoms As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

Compounds of the present invention can be prepared from commercially available starting materials or by the use of general synthetic techniques and procedures that are known to those skilled in the art. Outlined below are reaction schemes suitable for the preparation of such compounds. Further exemplification can be found in the specific examples detailed below.

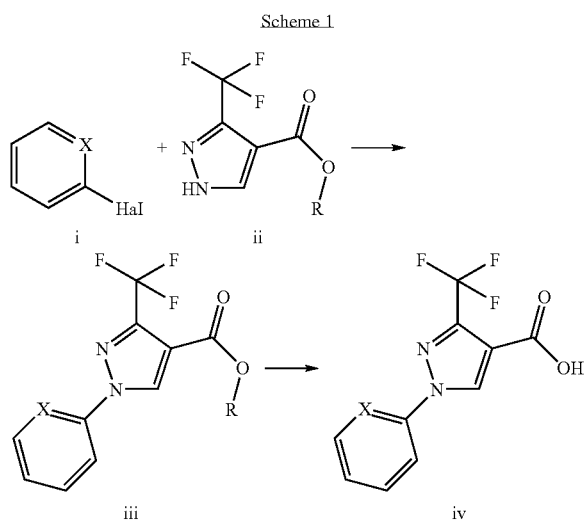

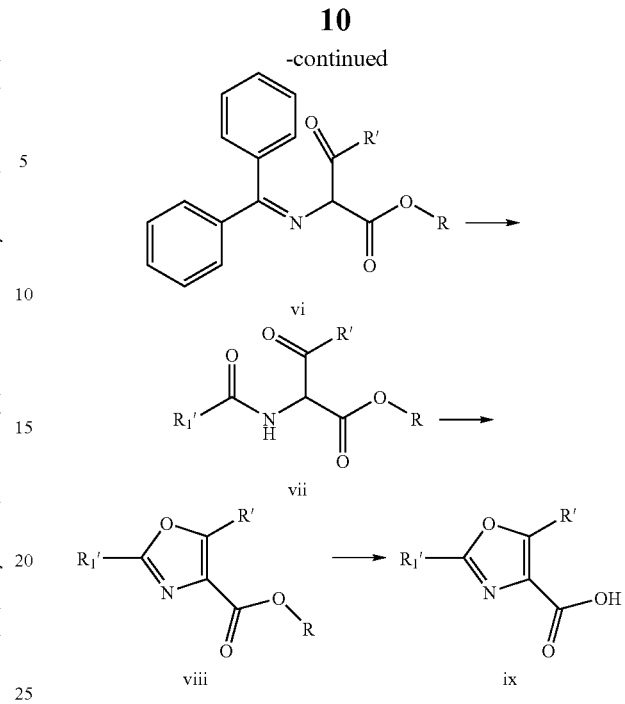

As shown in Scheme 1, an aryl halide i, where X=CH or N and 3-trifluoromethyl-1H-pyrazole-4-carboxylic acid ester ii, where R is lower alkyl, can be reacted using copper (I) iodide catalyst to give ester iii. The pyrazole ester iii can be hydrolyzed by treating with a base, typically lithium or sodium hydroxide in an aqueous/organic mixed solvent to give the pyrazole-4-carboxylic acid iv.

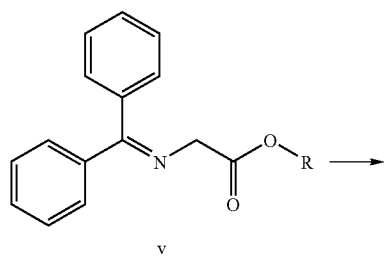

As shown in Scheme 2, oxazole compound ix can be prepared according to procedures similar to that described in *Org. Lett*, 2003, 5 (24), 4567. Compound v, commercially available or prepared according to the procedure described in *Bioorg. Med. Chem. Lett.* 2001, 11 (15), 1975, where R is lower alkyl, benzyl or other protecting groups, can be treated with a strong base, typically lithium bis(trimethylsilyl)amide, and an anhydride or an acid chloride, where R' can be a lower alkyl, cycloalkyl or heterocycloalkyl, in an appropriate solvent, typically tetrahydrofuran, to give the keto esters vi. The diphenyl imines vi can be hydrolyzed with 2N HCl aqueous solution in THF to give an amine HCl salt, which can be acylated with an acid chloride or an anhydride in presence of pyridine in an appropriate solvent, typically dichloromethane, to give compounds vii, where $R_1'$ is aryl, substituted aryl, heteroaryl, substituted heteroaryl, alkyl, or cycloalkyl. The oxazole ring can be generated by mixing compounds vii, triphenylphosphine and iodine in tetrahydrofuran with cooling. The oxazole esters viii can be hydrolyzed by treating with a base, typically lithium hydroxide in an aqueous/organic mixed solvent to give the oxazole-4-carboxylic acids ix.

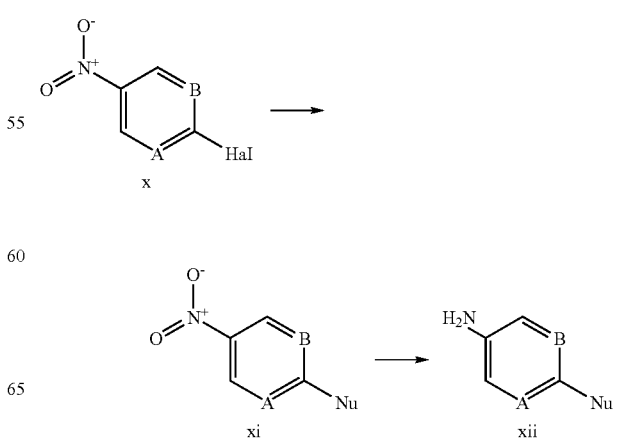

As shown in Scheme 3, commercially available nitro aryl halides x, where A and B can be CH or N and Hal is F, Cl or Br, can be treated with a nucleophile, typically an amine, and a neutralizing base, typically Et$_3$N, in an appropriate solvent, typically dichloromethane or N,N-dimethylformamide with or without heating to yield the corresponding substituted nitro aryls xi, where Nu can be a substituted or unsubstituted cyclic amine, such as pyrrolidine, piperidine, or piperazine. The nitro group in compounds xi can be reduced in an appropriate solvent, typically ethyl acetate or methanol under pressure of hydrogen, typically 50 psi, in presence of a catalyst; typically 10% palladium on carbon, or by SnCl$_2$ in HCl, to give substituted aryl amities xii.

In Scheme 4, compounds x (X and Y can be CH or N, Hal can be F, Cl, Br or I) can be treated with various cyclic amines in the presence of base and through nucleophilic aromatic substitution to give the corresponding nitro adducts (xiii) where R$_2$' and R$_3$' may be halogen, lower alkyl, haloalkyl, carboxyl, or carbalkoxy. The resulting nitro compounds can be reduced to the corresponding amines as in Scheme 3.

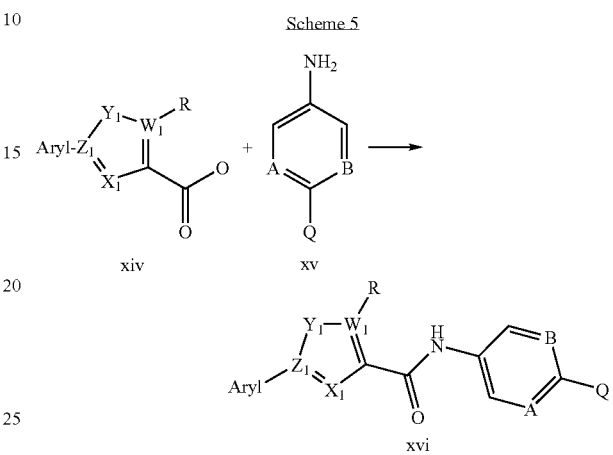

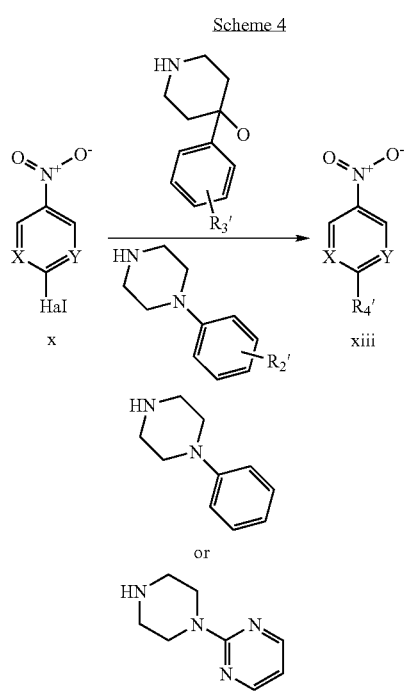

In Scheme 5, amide formation of an aryl-substituted five membered ring heterocyclic carboxylic acid, xiv, where Z$_1$ can be carbon or nitrogen, X$_1$ can be carbon or nitrogen and Y$_1$ can be oxygen, nitrogen, or carbon, W$_1$ can be carbon or S and R can be lower alkyl, fluorine substituted alkyl, alkoxy group or null when W$_1$ is S, with an aryl amine xv where A and B can be carbon or nitrogen and Q can be a substituted heterocycloaliphatic with or without an ether linkage, such as piperidine-4-carboxylate, 3-hydroxy-pyrrolidine-1-Boc, piperidine-1-Boc, or pyrrolidine-3-carboxylate, can be carried out by using general amide coupling methods such as acid chloride, mixed anhydride or coupling reagents. It is understood that a variety of coupling reagents such as BOP, PyBrop, or EDCI and HOBT may be used to yield amides xvi.

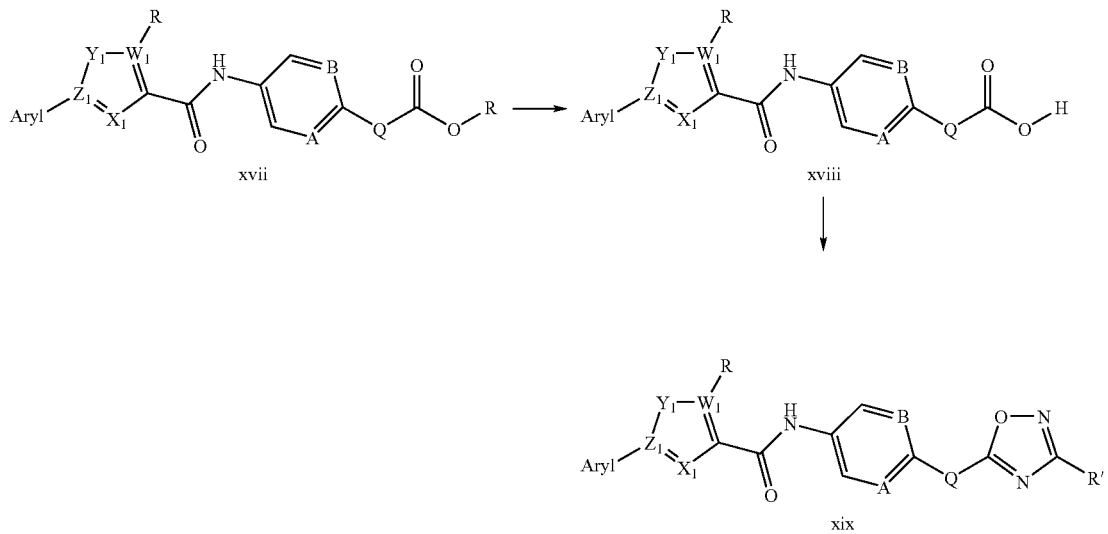

In Scheme 6, esters xvii, where $Z_1$ can be carbon or nitrogen, $X_1$ can be carbon or nitrogen and $Y_1$ can be oxygen, nitrogen, or carbon, $W_1$ can be carbon or S and R can be lower alkyl, fluorine substituted alkyl, alkoxy group or null, when $W_1$ is S, A and B can be carbon or nitrogen and Q can be a substituted heterocycloaliphatic as stated above, can be hydrolyzed to acids xviii by reacting with bases such as sodium, potassium or lithium hydroxide. Acids xviii can be converted to the corresponding acid chlorides and reacted with N-hydroxy alkyl amidines followed by TBAF to give oxadiazoles xix, where R' can be lower alkyl such as methyl, ethyl, isopropyl or cyclopropyl.

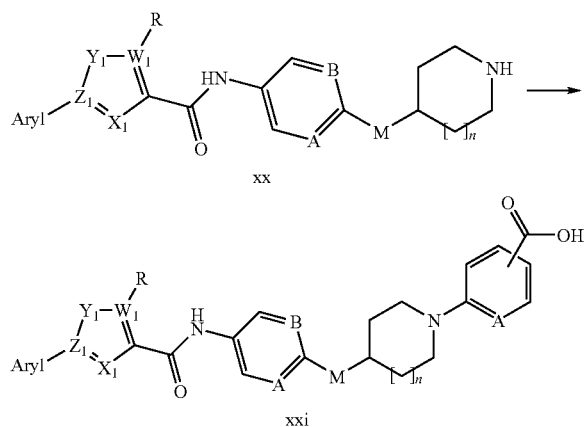

Scheme 7

In Scheme 7, amines xx, where $Z_1$ can be carbon or nitrogen, $X_1$ can be carbon or nitrogen and $Y_1$ can be oxygen, nitrogen, or carbon, $W_1$ can be carbon or S and R can be lower alkyl, fluorine substituted alkyl, alkoxy group or null, when $W_1$ is S, A and B can be carbon or nitrogen, n can be 0 or 1 and M can be oxygen or null, can be heated with halo aryl acids with an inorganic base such as potassium carbonate to give acids xxi.

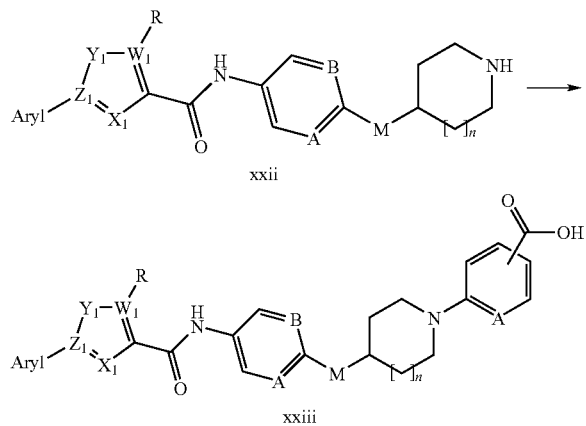

Scheme 8

In Scheme 8, amines xxii, where $Z_1$ can be carbon or nitrogen, $X_1$ can be carbon or nitrogen and $Y_1$ can be oxygen, nitrogen, or carbon, $W_1$ can be carbon or S and R can be lower alkyl, fluorine substituted alkyl, alkoxy group or null, when $W_1$ is S, A and B can be carbon or nitrogen, n can be 0 or 1 and M can be oxygen or null, can be heated with halo aryl acid esters in the presents of a strong base such as sodium tert-butoxide and a catalyst such as Pd2(dba)3 and a ligand such as X—PHOS, followed by ester hydrolysis to give acids xxiii.

EXAMPLES

The Examples which follow are for purposes of illustration and are not intended to limit the invention in any way.

General Methods:

Melting points were taken on a Thomas-Hoover apparatus and are uncorrected. Optical rotations were determined with a Perkin-Elmer model 241 polarimeter. 1H-NMR spectra were recorded with Varian XL-200, Mercury-300 or Unity-plus 400 MHz spectrometers. Tetramethylsilane (TMS) may be used as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230-400 mesh silica gel for flash chromatography; columns were run under a 0-5 psi head of nitrogen to assist flow. Thin layer chromatograms were run on glass thin layer plates coated with silica gel as supplied by E. Merck (E. Merck #1.05719) and were visualized by viewing under 254 nm UV light in a view box, by exposure to $I_2$ vapor, or by spraying with either phosphomolybdic acid (PMA) in aqueous ethanol, or after exposure to $Cl_2$, with a 4,4'-tetramethyldiamino-diphenylmethane reagent prepared according to E. Von Arx, M. Faupel and M Brugger, *J. Chromatography*, 1976, 220, 224-228.

Reversed phase high pressure liquid chromatography (RP-HPLC) was carried out using a Rainin HPLC employing a 41.4×300 mm, 8 □m, Dynamax™ C-18 column at a flow of 49 mL/min employing a gradient of acetonitrile:water (each containing 0.75% TFA) typically from 5 to 95% acetonitrile over 35-40 min. HPLC conditions are typically described in the format (5-95-35-214); this refers to a linear gradient of from 5% to 95% acetonitrile in water over 35 min while monitoring the effluent with a UV detector at a wavelength of 214 nm.

Preparative supercritical fluid chromatography (SFC) was performed on Berger MultiGram II Supercritical Fluid Chromatography system (Model SD-1) from Mettler-Toledo AutoChem Berger Instruments, Newark, Del., USA. The system consisted of an automatic liquid injection system with a DAICEL AD chiral column, 5 mL loop used to make injections and a thermal control module (TCM) used to control column temperature. Chromatographic conditions: SFC separations were performed at a temperature of 30° C., a flow rate of 70 mL/min, and $CO_2$ pressure of 100 bar. Knauer variable wavelength UV detector (supplied by Mettler-Toledo) with high pressure flow cell was used for SFC detection. Detection in SFC was performed by measurement of UV absorbance at 220 nm.

Methylene chloride (dichloromethane), 2-propanol, DMF, THF, toluene, hexane, ether, and methanol, were Fisher or Baker reagent grade and were used without additional purification except as noted, acetonitrile was Fisher or Baker HPLC grade and was used as is.

DEFINITIONS AS USED HEREIN

DGAT is diacylglycerol:acyl CoA O-acyltransferase,
THF is tetrahydrofuran,
DMF is N,N-dimethylformamide,
DMA is N,N-dimethylacetamide,
DMSO is dimethylsulfoxide, DCM is dichloromethane,
DME is dimethoxyethane,
MeOH is methanol,
EtOH is ethanol,
NaOH is sodium hydroxide,
NBS is N-bromosuccinimide,
TFA is 1,1,1-trifluoroacetic acid,
HOBT is 1-hydroxybenzotriazole,
BOP is (benzotriazol-1-yloxy)tris(dimethylamino)phosphonium hexafluorophosphate,
PyBroP is bromotripyrrolidinophosphonium hexafluorophosphate,
EDCI is 1-[3-(dimethylamino)propyl]-3-ethylcarbodiimide hydrochloride,
DIPEA is diisopropylethylamine,
X-PHOS is (2',4',6'-triisopropyl-1,1'-biphenyl-2-yl)dicyclohexylphosphine,
Pd2(dba)3 is tris(dibenzylideneacetone)dipalladium,
brine is saturated aqueous sodium chloride solution,
DAG is 1,2-dioleoyl-sn-glycerol,
TLC is thin layer chromatography,
RP HPLC is reversed phase high performance liquid chromatography,
APCI-MS is atmospheric pressure chemical ionization mass spectrometry,
ES-MS is electrospray mass spectrometry,
LCMS is liquid chromatography mass spectrometry,
RT is room or ambient temperature.

Silica gel chromatography on Biotage columns refers to use of a flash chromatography system supplied by the Biotage Division of the Dyax Corporation employing prepacked 40 g (40 s columns), 90 g (40 m columns) or 800 g (75 m columns). Elution is carried out with hexane-ethyl acetate mixtures under 10-15 psi nitrogen pressure.

Part I

Preparation of Preferred Intermediates

Preparation of 1-phenyl-3-trifluoromethyl-1H-pyrazole-4-carboxylic acid

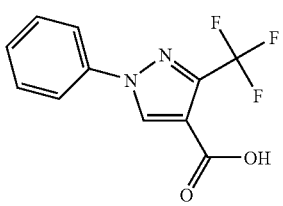

A mixture of 3-trifluoromethyl-1H-pyrazole-4-carboxylic acid ethyl ester (2.5 g, 12.0 mmol), copper (I) iodide (0.69 g, 3.6 mmol) and potassium carbonate (3.49 g, 25.3 mmol) in toluene (12 mL) in a round bottom flask was purged with argon. To the reaction mixture was then added iodobenzene (1.61 mL, 14.4 mmol) and racemic trans-N,N'-dimethyl-cyclohexane-1,2-diamine (1.16 mL, 7.2 mmol). The slurry was heated under Ar in an oil bath at 110° C. for 24 hours. After cooling to room temperature, the reaction mixture was diluted with ethyl acetate and filtered over a bed of celite. The organic washings were combined and concentrated to give a crude which was purified by silica gel chromatography (Isco 120 g column, 0→30% ethyl acetate/hexanes) to give 1-phenyl-3-trifluoromethyl-1H-pyrazole-4-carboxylic acid ethyl ester (2.91 g, 85%) as an off-white solid. The NMR spectrum obtained on the sample is compatible with its structure.

A mixture of 1-phenyl-3-trifluoromethyl-1H-pyrazole-4-carboxylic acid ethyl ester (1.25 g, 4.4 mmol) and 1N aqueous sodium hydroxide solution (17.3 mL) in methanol (20 mL) was stirred at room temperature overnight. The reaction mixture was concentrated and acidified to pH ~1 with 1N aqueous hydrochloric acid. The slurry was extracted with methylene chloride and the combined organic layers were washed with saturated sodium chloride and dried over sodium sulfate. Filtration and concentration gave 1-phenyl-3-trifluoromethyl-1H-pyrazole-4-carboxylic acid (1 g, 89% yield) as an off-white solid, which was directly used in the next step without further purification. LCMS calcd for C11H7F3N2O2 (m/e) 256, obsd 255 (M−H).

Preparation of 1-pyridin-2-yl-3-trifluoromethyl-1H-pyrazole-4-carboxylic acid

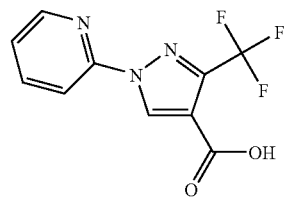

With a method similar to that used for the preparation of 1-phenyl-3-trifluoromethyl-1H-pyrazole-4-carboxylic acid above, 1-pyridin-2-yl-3-trifluoromethyl-1H-pyrazole-4-carboxylic acid was prepared from 3-trifluoromethyl-1H-pyrazole-4-carboxylic acid ethyl ester and 2-chloropyridine followed by ester hydrolysis. LCMS calcd for C10H6F3N3O2 (m/e) 257, obsd 258 (M+H).

Preparation of 4-(3-trifluoromethyl-phenyl)-3,4,5,6-tetrahydro-2H-[1,2]bipyridinyl-5'-ylamine

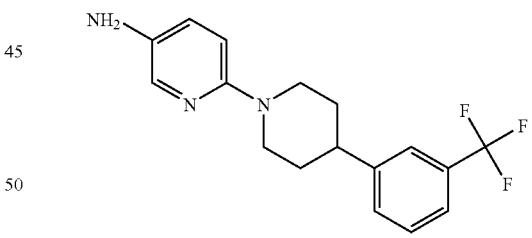

To a mixture of 2-chloro-5-nitropyridine (500 mg, 3.2 mmol) and 4-(3-trifluoromethyl-phenyl)-piperidine hydrochloride in DMF (15 mL) was added diisopropylethylamine (1.70 mL, 9.60 mmol). The mixture was heated in a sealed tube at 80° C. for 24 hours. The mixture was concentrated to dryness and triturated in methanol to give 5'-nitro-4-(3-trifluoromethyl-phenyl)-3,4,5,6-tetrahydro-2H-[1,2']bipyridinyl. The NMR spectrum obtained on the sample is compatible with its structure.

To a solution of 5'-nitro-4-(3-trifluoromethyl-phenyl)-3,4,5,6-tetrahydro-2H-[1,2']bipyridinyl (500 mg, 1.42 mmol) from above in ethanol (15 mL) was added 10% palladium on carbon (100 mg). The mixture was hydrogenated at 50 psi for 2 hr. The mixture was filtered over celite and the solvents were evaporated to give 4-(3-trifluoromethyl-phenyl)-3,4,5,6-tetrahydro-2H-[1,2']bipyridinyl-5'-ylamine that was used in the next step with further purification. LCMS calcd for C17H18F3N3 (m/e) 321, obsd 322 (M+H).

Preparation of 4-[4-(5-amino-pyridin-2-yl)-piperazin-1-yl]-benzoic acid ethyl ester

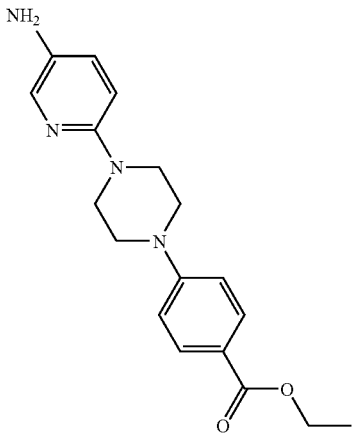

With a method similar to that used for the preparation of 4-(3-trifluoromethyl-phenyl)-3,4,5,6-tetrahydro-2H-[1,2'] bipyridinyl-5'-ylamine above, 4-[4-(5-amino-pyridin-2-yl)-piperazin-1-yl]-benzoic acid ethyl ester was prepared from 2-chloro-5-nitropyridine and 4-piperazin-1-yl-benzoic acid ethyl ester followed by hydrogenation. LCMS calcd for C18H22N4O2 (m/e) 326, obsd 327 (M+H).

Preparation of 6-[4-(4-trifluoromethyl-phenyl)-piperazin-1-yl]-pyridin-3-ylamine

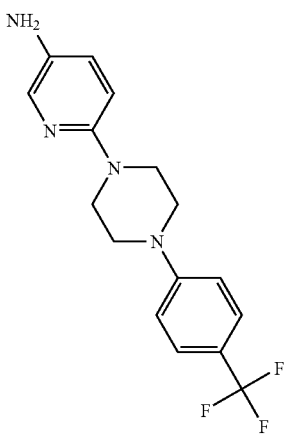

With a method similar to that used for the preparation of 4-(3-trifluoromethyl-phenyl)-3,4,5,6-tetrahydro-2H-[1,2'] bipyridinyl-5'-ylamine above, 6-[4-(4-trifluoromethyl-phenyl)-piperazin-1-yl]-pyridin-3-ylamine was prepared from 2-chloro-5-nitropyridine and 1-(4-trifluoromethyl-phenyl)-piperazine followed by hydrogenation. LCMS calcd for C16H17F3N4 (m/e) 322, obsd 323 (M+H).

Preparation of 6-[4-(4-methoxy-phenyl)-piperazin-1-yl]-pyridin-3-ylamine

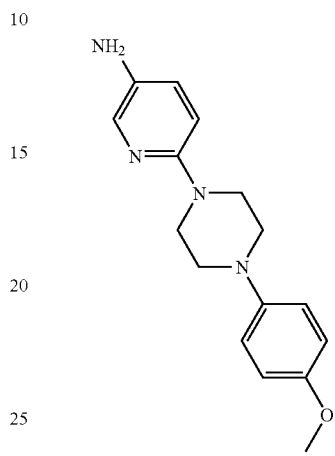

With a method similar to that used for the preparation of 4-(3-trifluoromethyl-phenyl)-3,4,5,6-tetrahydro-2H-[1,2'] bipyridinyl-5'-ylamine above, 6-[4-(4-methoxy-phenyl)-piperazin-1-yl]-pyridin-3-ylamine was prepared from 2-chloro-5-nitropyridine and 1-(4-methoxy-phenyl)-piperazine followed by hydrogenation. LCMS calcd for C16H20N4O (m/e) 284, obsd 285 (M+H).

Preparation of 6-[4-(2-trifluoromethyl-phenyl)-piperazin-1-yl]-pyridin-3-ylamine

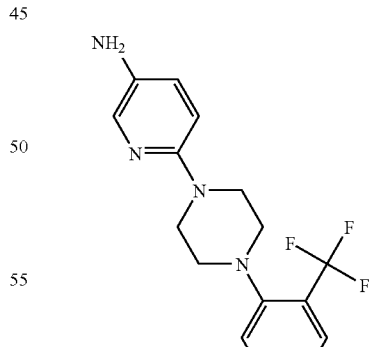

With a method similar to that used for the preparation of 4-(3-trifluoromethyl-phenyl)-3,4,5,6-tetrahydro-2H-[1,2'] bipyridinyl-5'-ylamine above, 6-[4-(2-trifluoroethyl-phenyl)-piperazin-1-yl]-pyridin-3-ylamine was prepared from 2-chloro-5-nitropyridine and 1-(2-trifluoromethyl-phenyl)-piperazine followed by hydrogenation. LCMS calcd for C16H17F3N4 (m/e) 322, obsd 323 (M+H).

Preparation of 6-[4-(3-trifluoromethyl-phenyl)-piperazin-1-yl]-pyridin-3-ylamine

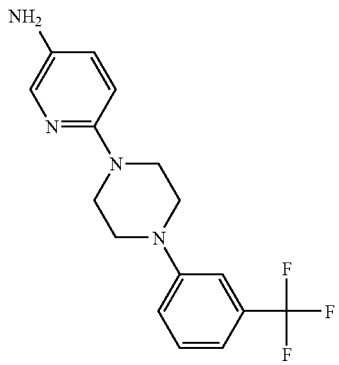

With a method similar to that used for the preparation of 4-(3-trifluoromethyl-phenyl)-3,4,5,6-tetrahydro-2H-[1,2'] bipyridinyl-5'-ylamine above, 6-[4-(3-trifluoromethyl-phenyl)-piperazin-1-yl]-pyridin-3-yl amine was prepared from 2-chloro-5-nitropyridine and 1-(3-trifluoromethyl-phenyl)-piperazine followed by hydrogenation. LCMS calcd for C16H17F3N4 (m/e) 322, obsd 323 (M+H).

Preparation of 6-[4-(3-methoxy-phenyl)-piperazin-1-yl]-pyridin-3-ylamine

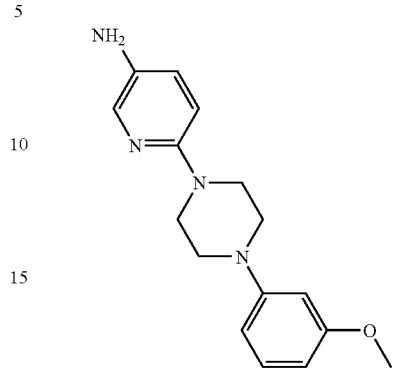

With a method similar to that used for the preparation of 4-(3-trifluoromethyl-phenyl)-3,4,5,6-tetrahydro-2H-[1,2'] bipyridinyl-5'-ylamine above, 6-[4-(3-methoxy-phenyl)-piperazin-1-yl]-pyridin-3-ylamine was prepared from 2-chloro-5-nitropyridine and 1-(3-methoxy-phenyl)-piperazine followed by hydrogenation. LCMS calcd for C16H20N4O (m/e) 284, obsd 285 (M+H).

Preparation of 6-[4-(2-methoxy-phenyl)-piperazin-1-yl]-pyridin-3-ylamine

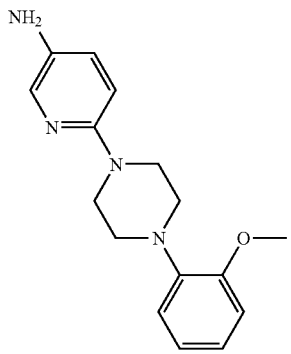

With a method similar to that used for the preparation of 4-(3-trifluoromethyl-phenyl)-3,4,5,6-tetrahydro-2H-[1,2'] bipyridinyl-5'-ylamine above, 6-[4-(2-methoxy-phenyl)-piperazin-1-yl]-pyridin-3-ylamine was prepared from 2-chloro-5-nitropyridine and 1-(2-methoxy-phenyl)-piperazine followed by hydrogenation. LCMS calcd for C16H20N4O (m/e) 284, obsd 285 (M+H).

Preparation of 5'-amino-4-(3-trifluoromethyl-phenyl)-3,4,5,6-tetrahydro-2H-[1,2']bipyridinyl-4-ol

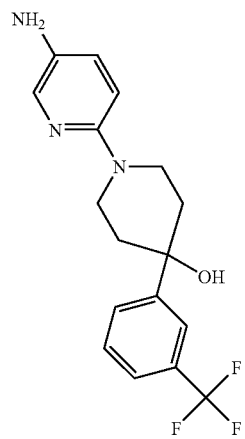

With a method similar to that used for the preparation of 4-(3-trifluoromethyl-phenyl)-3,4,5,6-tetrahydro-2H-[1,2'] bipyridinyl-5'-ylamine above, 5'-amino-4-(3-trifluoromethyl-phenyl)-3,4,5,6-tetrahydro-2H-[1,2']bipyridinyl-4-ol was prepared from 2-chloro-5-nitropyridine and 4-(3-trifluoromethyl-phenyl)-piperidin-4-ol followed by hydrogenation. LCMS calcd for C17H18F3N3O (m/e) 337, obsd 338 (M+H).

Preparation of 6-(4-phenyl-piperazin-1-yl)-pyridin-3-ylamine

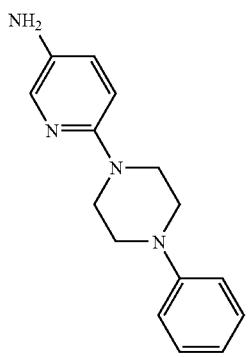

With a method similar to that used for the preparation of 4-(3-trifluoromethyl-phenyl)-3,4,5,6-tetrahydro-2H-[1,2']bipyridinyl-5'-ylamine above, 6-(4-phenyl-piperazin-1-yl)-pyridin-3-ylamine was prepared from 2-chloro-5-nitropyridine and 1-phenyl-piperazine followed by hydrogenation. LCMS calcd for C15H18N4 (m/e) 254, obsd 255 (M+H).

Preparation of 5'-amino-4-phenyl-3,4,5,6-tetrahydro-2H-[1,2']bipyridinyl-4-ol

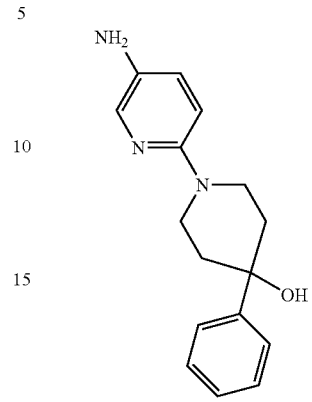

With a method similar to that used for the preparation of 4-(3-trifluoromethyl-phenyl)-3,4,5,6-tetrahydro-2H-[1,2']bipyridinyl-5'-ylamine above, 5'-amino-4-phenyl-3,4,5,6-tetrahydro-2H-[1,2']bipyridinyl-4-ol was prepared from 2-chloro-5-nitropyridine and 4-phenyl-piperidin-4-ol followed by hydrogenation. LCMS calcd for C16H19N3O (m/e) 269, obsd 270 (M+H).

Preparation of 4-phenyl-3,4,5,6-tetrahydro-2H-[1,2']bipyridinyl-5'-ylamine

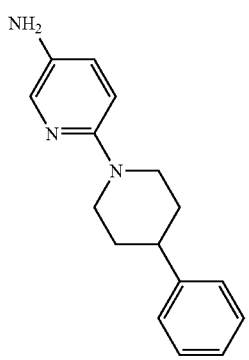

With a method similar to that used for the preparation of 4-(3-trifluoromethyl-phenyl)-3,4,5,6-tetrahydro-2H-[1,2']bipyridinyl-5'-ylamine above, 4-phenyl-3,4,5,6-tetrahydro-2H-[1,2']bipyridinyl-5'-ylamine was prepared from 2-chloro-5-nitropyridine and 4-phenyl-piperidine followed by hydrogenation. LCMS calcd for C16H19N3 (m/e) 253, obsd 254 (M+H).

Preparation of 4-(3-trifluoromethyl-phenyl)-3,4,5,6-tetrahydro-2H-[1,2']bipyridinyl-5'-ylamine

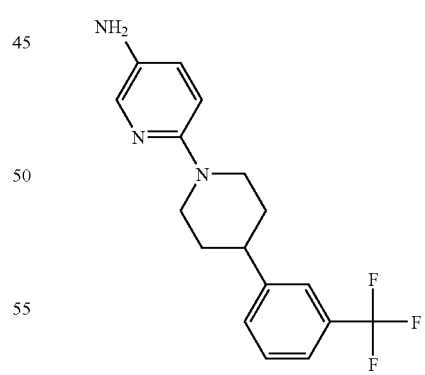

With a method similar to that used for the preparation of 4-(3-trifluoromethyl-phenyl)-3,4,5,6-tetrahydro-2H-[1,2']bipyridinyl-5'-ylamine above, 4-(3-trifluoromethyl-phenyl)-3,4,5,6-tetrahydro-2H-[1,2']bipyridinyl-5'-ylamine was prepared from 2-chloro-5-nitropyridine and 4-(3-trifluoromethyl-phenyl)-piperidine followed by hydrogenation. LCMS calcd for C17H18F3N3 (m/e) 321, obsd 322 (M+H).

Preparation of 6-[4-(4-fluoro-phenyl)-piperazin-1-yl]-pyridin-3-ylamine

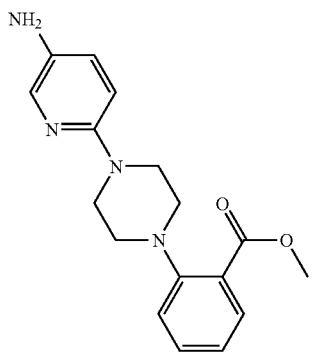

With a method similar to that used for the preparation of 4-(3-trifluoromethyl-phenyl)-3,4,5,6-tetrahydro-2H-[1,2']bipyridinyl-5'-ylamine above, 6-[4-(4-fluoro-phenyl)-piperazin-1-yl]-pyridin-3-ylamine was prepared from 2-chloro-5-nitropyridine and 1-(4-fluoro-phenyl)-piperazine followed by hydrogenation. LCMS calcd for C15H17FN4 (m/e) 272, obsd 273 (M+H).

Preparation of 2-[4-(5-amino-pyridin-2-yl)-piperazin-1-yl]-benzoic acid methyl ester

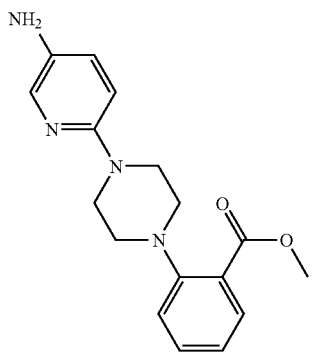

With a method similar to that used for the preparation of 4-(3-trifluoromethyl-phenyl)-3,4,5,6-tetrahydro-2H-[1,2']bipyridinyl-5'-ylamine above, 2-[4-(5-amino-pyridin-2-yl)-piperazin-1-yl]-benzoic acid methyl ester was prepared from 2-chloro-5-nitropyridine and 2-piperazin-1-yl-benzoic acid methyl ester followed by hydrogenation. LCMS calcd for C17H20N4O2 (m/e) 312, obsd 313 (M+H).

Preparation of 3-[4-(5-amino-pyridin-2-yl)-piperazin-1-yl]-benzoic acid ethyl ester

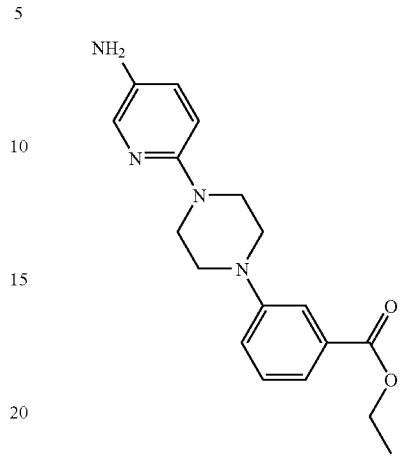

With a method similar to that used for the preparation of 4-(3-trifluoromethyl-phenyl)-3,4,5,6-tetrahydro-2H-[1,2']bipyridinyl-5'-ylamine above, 3-[4-(5-amino-pyridin-2-yl)-piperazin-1-yl]-benzoic acid ethyl ester was prepared from 2-chloro-5-nitropyridine and 3-piperazin-1-yl-benzoic acid ethyl ester followed by hydrogenation. LCMS calcd for C18H22N4O2 (m/e) 326, obsd 327 (M+H).

Preparation of 6-(4-pyrimidin-2-yl-piperazin-1-yl)-pyridin-3-ylamine

To a mixture of 2-chloro-5-nitropyridine (500 mg, 3.2 mmol) and 2-piperazin-1-yl-pyrimidine (520 mg, 3.2 mmol) in DMF (15 mL) was added diisopropylethylamine (2.70 mL, 15.5 mmol). The mixture was heated in a sealed tube at 80° C. for 24 hours. The mixture was concentrated to dryness and triturated in methanol to give 2-[4-(5-nitro-pyridin-2-yl)-piperazin-1-yl]-pyrimidine. The NMR spectrum on this sample is compatible with its structure.

To a solution of 2-[4-(5-nitro-pyridin-2-yl)-piperazin-1-yl]-pyrimidine (600 mg, 2.1 mmol) from above in 2N hydrochloric acid (7.50 mL) was added SnCl$_2$ (1.60 g, 8.4 mmol). The mixture was stirred at room temperature for 2 hr. The mixture was evaporated to dryness and basified with 1N NaOH. The crude solid was triturated in methanol to afford 6-(4-pyrimidin-2-yl-piperazin-1-yl)-pyridin-3-ylamine as a yellow solid. The NMR spectrum obtained on the sample is compatible with its structure. LCMS calcd for C13H16N6 (m/e) 256, obsd 257 (M+H).

Preparation of 1-(4-amino-phenyl)-piperidine-4-carboxylic acid ethyl ester

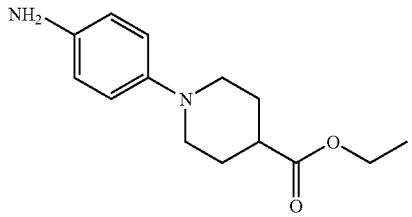

A solution of 1-fluoro-4-nitrobenzene (2.0 g, 1.50 mL, 14 mmol), piperidine-4-carboxylic acid ethyl ester (2.2 g, 2.15 mL, 14 mmol), and potassium carbonate (9.7 g, 70 mmol) in $CH_3CN$ (20 mL) was stirred at room temperature overnight. The resulting mixture was filtered and concentrated. The residue was purified by chromatography on silica gel (gradient elution with 5-50% ethyl acetate in hexanes) to produce 2.0 g of 1-(4-nitro-phenyl)-piperidine-4-carboxylic acid ethyl ester as a yellow solid. 1.0 g of the above 1-(4-nitro-phenyl)-piperidine-4-carboxylic acid ethyl ester was hydrogenated using 10% Pd/C (200 mg) in MeOH, under 50 psi pressure of hydrogen for 2 hours. The catalyst was filtered, and the residue was concentrated to produce 1-(4-amino-phenyl)-piperidine-4-carboxylic acid ethyl ester. This material was directly used in the next step without further purification.

Preparation of 1-(5-amino-pyrimidin-2-yl)-piperidine-4-carboxylic acid ethyl ester

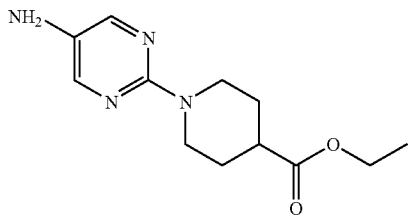

With a method similar to that used for the preparation of 1-(4-nitro-phenyl)-piperidine-4-carboxylic acid ethyl ester above, 1-(5-nitro-pyrimidin-2yl)-piperidine-4-carboxylic acid ethyl ester was prepared from 2-chloro-5-nitro-pyrimidine (2.0 g, 12.5 mmol), piperidine-4-carboxylic acid ethyl ester (1.97 g, 1.93 mL, 12.5 mmol), and potassium carbonate (8.64 g, 62.5 mmol). With a method similar to that used for the preparation of 1-(4-amino-phenyl)-piperidine-4-carboxylic acid ethyl ester above, 1-(5-amino-pyrimidin-2-yl)-piperidine-4-carboxylic acid ethyl ester was prepared by the hydrogenation of 1-(5-nitro-pyrimidin-2-yl)-piperidine-4-carboxylic acid ethyl ester (10% Pd/C, 50 psi, MeOH). This material was directly used in the next step without further purification.

Preparation of 5'-amino-3,4,5,6-tetrahydro-2H-[1,2'] bipyridinyl-4-carboxylic acid ethyl ester

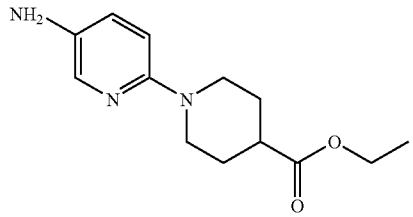

With a method similar to that used for the preparation of 1-(4-amino-phenyl)-piperidine-4-carboxylic acid ethyl ester above, 5'-amino-3,4,5,6-tetrahydro-2H-[1,2']bipyridinyl-4-carboxylic acid ethyl ester was prepared by the hydrogenation of commercially available ethyl 1-(5-nitro-2-pyridinyl)-4-piperidine carboxylate (10% Pd/C, 50 psi, MeOH). This material was directly used in the next step without further purification.

Preparation of 1-(5-amino-pyridin-2-yl)-pyrrolidine-3-carboxylic acid methyl ester

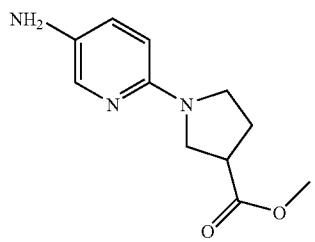

With a method similar to that used for the preparation of 1-(4-nitro-phenyl)-piperidine-4-carboxylic acid ethyl ester above, 1-(5-nitro-pyridin-2-yl)-pyrrolidine-3-carboxylic acid methyl ester was prepared from 2-chloro-5-nitro-pyridine, pyrrolidine-3-carboxylic acid methyl ester, and potassium carbonate (under reflux). With a method similar to that used for the preparation of 1-(4-amino-phenyl)-piperidine-4-carboxylic acid ethyl ester above, 1-(5-amino-pyridin-2-yl)-pyrrolidine-3-carboxylic acid methyl ester was prepared by the hydrogenation of 1-(5-nitro-pyridin-2-yl)-pyrrolidine-3-carboxylic acid methyl ester (10% Pd/C, 50 psi, MeOH). This material was directly used in the next step without further purification.

Preparation of 1-{4-[(2-phenyl-5-trifluoromethyl-oxazole-4-carbonyl)-amino]-phenyl}-piperidine-4-carboxylic acid ethyl ester

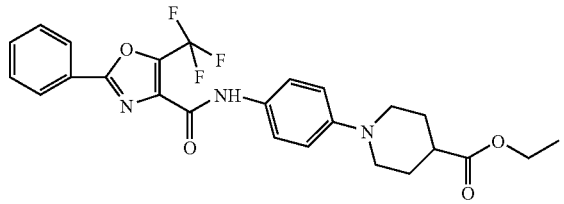

A mixture of 2-phenyl-5-trifluoromethyl-oxazole-4-carboxylic acid (926 mg, 3.6 mmol), triethylamine (910 mg, 1.25 mL, 9.0 mmol), bromotripyrrolidinophosphonium hexafluorophosphate (PyBroP, 2.51 g, 5.4 mmol) and 1-(4-aminophenyl)-piperidine-4-carboxylic acid ethyl ester (3.6 mmol, prepared above) in DMF (10 mL) was stirred at room temperature overnight. The reaction mixture was diluted with EtOAc, and washed twice with water. The organic phase was then dried over $Na_2SO_4$, filtered, and concentrated. The residue was purified by chromatography on silica gel (gradient elution with 10-50% ethyl acetate in hexanes) to provide 1-{4-[(2-phenyl-5-trifluoromethyl-oxazole-4-carbonyl)-amino]-phenyl}-piperidine-4-carboxylic acid ethyl ester. HRMS calcd for $C_{25}H_{24}F_3N_3O_4$ (M+H) 488.1792, obsd 488.1792.

Preparation of 5'-[(2-phenyl-5-trifluoromethyl-oxazole-4-carbonyl)-amino]-3,4,5,6-tetrahydro-2H-[1,2']bipyridinyl-4-carboxylic acid ethyl ester

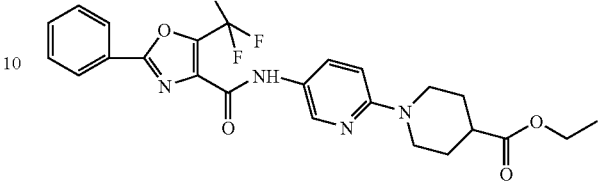

With a method similar to that used for the preparation of 1-{4-[(2-phenyl-5-trifluoromethyl-oxazole-4-carbonyl)-amino]-phenyl}-piperidine-4-carboxylic acid ethyl ester above, 5'-[(2-phenyl-5-trifluoromethyl-oxazole-4-carbonyl)-amino]-3,4,5,6-tetrahydro-2H-[1,2']bipyridinyl-4-carboxylic acid ethyl ester was prepared from 2-phenyl-5-trifluoromethyl-oxazole-4-carboxylic acid and 5'-amino-3,4,5,6-tetrahydro-2H-[1,2']bipyridinyl-4-carboxylic acid ethyl ester. LCMS calcd for $C_{24}H_{23}F_3N_4O_4$ (m/e) 488.46, obsd 489.17 (M+H).

Preparation of 1-{5-[(2-phenyl-5-trifluoromethyl-oxazole-4-carbonyl)-amino]-pyrimidin-2-yl}-piperidine-4-carboxylic acid ethyl ester

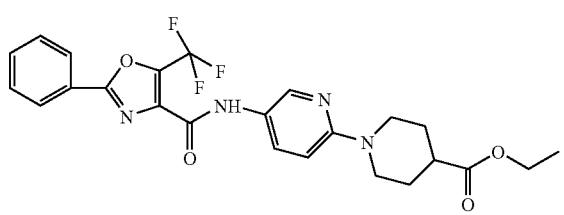

With a method similar to that used for the preparation of 1-{4-[(2-phenyl-5-trifluoromethyl-oxazole-4-carbonyl)-amino]-phenyl}-piperidine-4-carboxylic acid ethyl ester above, 1-{5-[(2-phenyl-5-trifluoromethyl-oxazole-4-carbonyl)-amino]-piperidin-2-yl}-piperidine-4-carboxylic acid ethyl ester was prepared from 2-phenyl-5-trifluoromethyl-oxazole-4-carboxylic acid (1.2 equivalents) and 1-(5-amino-piperidin-2-yl)-piperidine-4-carboxylic acid ethyl ester. HRMS calcd for $C_{23}H_{22}F_3N_5O_4$ (M+H) 490.1697, obsd 490.1695.

Preparation of 1-{5-[(2-phenyl-5-trifluoromethyl-oxazole-4-carbonyl)-amino]-pyridin-2-yl}-pyrrolidine-3-carboxylic acid methyl ester

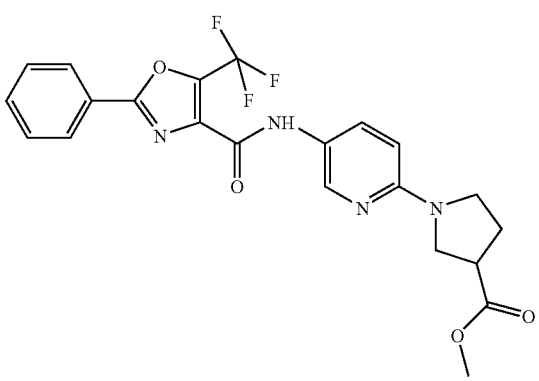

With a method similar to that used for the preparation of 1-{4-[(2-phenyl-5-trifluoromethyl-oxazole-4-carbonyl)-amino]-phenyl}-piperidine-4-carboxylic acid ethyl ester above, 1-{5-[(2-phenyl-5-trifluoromethyl-oxazole-4-carbonyl)-amino]-pyridin-2-yl}-pyrrolidine-3-carboxylic acid methyl ester was prepared from 2-phenyl-5-trifluoromethyl-oxazole-4-carboxylic acid and 1-(5-amino-pyridin-2-yl)-pyrrolidine-3-carboxylic acid methyl ester.

Preparation of 5'-{[2-(2-trifluoromethoxy-phenyl)-5-trifluoromethyl-oxazole-4-carbonyl]-amino}-3,4,5,6-tetrahydro-2H-[1,2']bipyridinyl-4-carboxylic acid ethyl ester

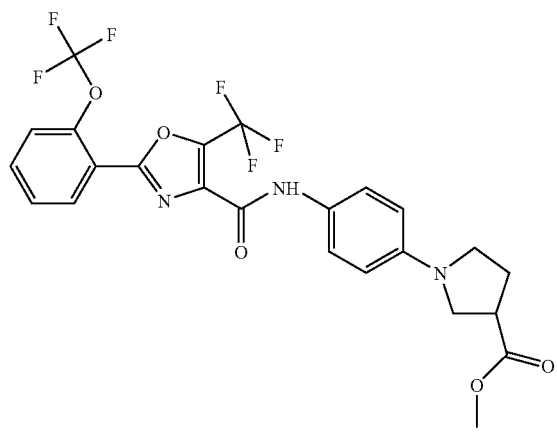

With a method similar to that used for the preparation of 1-{4-[(2-phenyl-5-trifluoromethyl-oxazole-4-carbonyl)-amino]-phenyl}-piperidine-4-carboxylic acid ethyl ester above, 5'-{[2-(2-trifluoromethoxy-phenyl)-5-trifluoromethyl-oxazole-4-carbonyl]-amino}-3,4,5,6-tetrahydro-2H-[1,2']bipyridinyl-4-carboxylic acid ethyl ester was prepared from 2-(2-trifluoromethoxy-phenyl)-5-trifluoromethyl-oxazole-4-carboxylic acid and 5'-amino-3,4,5,6-tetrahydro-2H-[1,2']bipyridinyl-4-carboxylic acid ethyl ester.

Preparation of 1-{4-[(2-phenyl-5-trifluoromethyl-oxazole-4-carbonyl)-amino]-phenyl}-piperidine-4-carboxylic acid

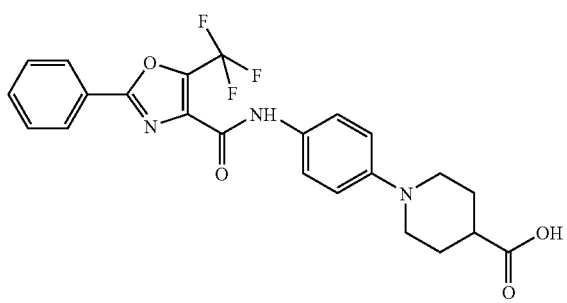

A solution of 1-{4-[(2-phenyl-5-trifluoromethyl-oxazole-4-carbonyl)-amino]-phenyl}-piperidine-4-carboxylic acid ethyl ester (1.1 g, 2.3 mmol) in 20 mL of MeOH was treated with 2.8 mL (5.6 mmol) of 2 N NaOH, and the reaction mixture was stirred at room temperature overnight. The resulting mixture was then concentrated to remove most of the MeOH solvent. The residue was then neutralized with concentrated HCl. A white precipitate formed. The product was then collected by filtration, washed with water, triturated with ether, and dried to furnish 0.82 g of 1-{4-[(2-phenyl-5-trifluoromethyl-oxazole-4-carbonyl)-amino]-phenyl}-piperidine-4-carboxylic acid. This material was used in the next step without further purification.

Preparation of 5'-[(2-phenyl-5-trifluoromethyl-oxazole-4-carbonyl)-amino]-3,4,5,6-tetrahydro-2H-[1,2']bipyridinyl-4-carboxylic acid

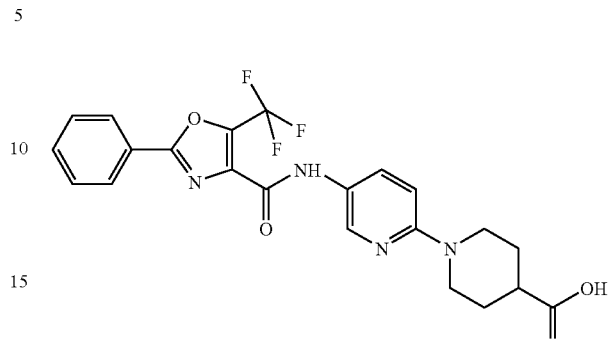

With a similar method to that used for the preparation of 1-{4-[(2-phenyl-5-trifluoromethyl-oxazole-4-carbonyl)-amino]-phenyl}-piperidine-4-carboxylic acid above, 5'-[(2-phenyl-5-trifluoromethyl-oxazole-4-carbonyl)-amino]-3,4,5,6-tetrahydro-2H-[1,2']bipyridinyl-4-carboxylic acid was prepared from 5'-[(2-phenyl-5-trifluoromethyl-oxazole-4-carbonyl)-amino]-3,4,5,6-tetrahydro-2H-[1,2']bipyridinyl-4-carboxylic acid ethyl ester (2.3 g, 4.7 mmol) and 2 N sodium hydroxide (14.1 mmol, 7.05 mL). This material was used in the next step without further purification.

Preparation of 1-{5-[(2-phenyl-5-trifluoromethyl-oxazole-4-carbonyl)-amino]-pyrimidin-2-yl}-piperidine-4-carboxylic acid

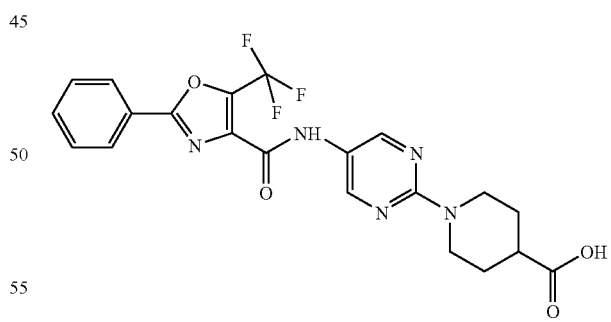

With a similar method to that used for the preparation of 1-{4-[(2-phenyl-5-trifluoromethyl-oxazole-4-carbonyl)-amino]-phenyl}-piperidine-4-carboxylic acid above, 1-{5-[(2-phenyl-5-trifluoromethyl-oxazole-4-carbonyl)-amino]-pyrimidin-2-yl}-piperidine-4-carboxylic acid was prepared from 1-{5-[(2-phenyl-5-trifluoromethyl-oxazole-4-carbonyl)-amino]-piperidin-2-yl}-piperidine-4-carboxylic acid ethyl ester and 2 N sodium hydroxide. This material was used in the next step without further purification.

Preparation of 5'-{[2-(2-trifluoromethoxy-phenyl)-5-trifluoromethyl-oxazole-4-carbonyl]-amino}-3,4,5,6-tetrahydro-2H-[1,2']bipyridinyl-4-carboxylic acid

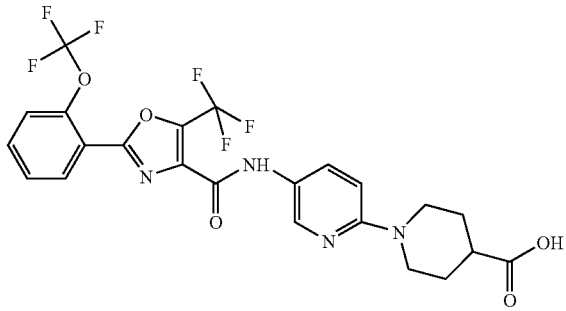

With a similar method to that used for the preparation of 1-{4-[(2-phenyl-5-trifluoromethyl-oxazole-4-carbonyl)-amino]-phenyl}-piperidine-4-carboxylic acid above, 5'-{[2-(2-trifluoromethoxy-phenyl)-5-trifluoromethyl-oxazole-4-carbonyl]-amino}-3,4,5,6-tetrahydro-2H-[1,2']bipyridinyl-4-carboxylic acid was prepared from 5'-{[2-(2-trifluoromethoxy-phenyl)-5-trifluoromethyl-oxazole-4-carbonyl]-amino}-3,4,5,6-tetrahydro-2H-[1,2']bipyridinyl-4-carboxylic acid ethyl ester and 2 N sodium hydroxide. This material was used in the next step without farther purification.

Preparation of 1-{5-[(2-phenyl-5-trifluoromethyl-oxazole-4-carbonyl)-amino]-pyridin-2-yl}-pyrrolidine-3-carboxylic acid

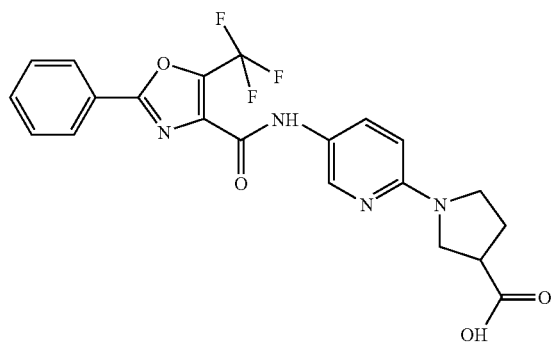

With a similar method to that used for the preparation of 1-{4-[(2-phenyl-5-trifluoromethyl-oxazole-4-carbonyl)-amino]-phenyl}-piperidine-4-carboxylic acid above, 1-{5-[(2-phenyl-5-trifluoromethyl-oxazole-4-carbonyl)-amino]-pyridin-2-yl}-pyrrolidine-3-carboxylic acid was prepared from 1-{5-[(2-phenyl-5-trifluoromethyl-oxazole-4-carbonyl)-amino]-pyridin-2-yl}-pyrrolidine-3-carboxylic acid methyl ester and 2 N sodium hydroxide. This material was used in the next step without further purification.

2-Phenyl-5-trifluoromethyl-oxazole-4-carboxylic acid (4-piperidin-4-yl-phenyl)-amide

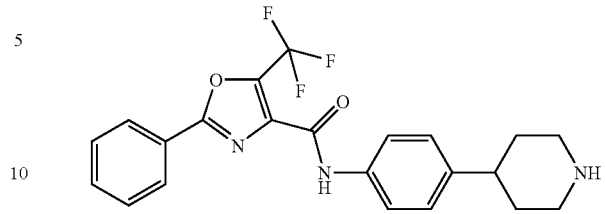

A mixture of 2-phenyl-5-trifluoromethyl-oxazole-4-carboxylic acid (10.0 g, 39.0 mmol), methylene chloride (500 mL), and a catalytic amount of DMF (0.2 mL) was stirred under argon, and oxalyl chloride (2M in methylene chloride, 50 mL, 100 mmol) was added dropwise into the mixture over 30 min. The mixture was stirred at room temperature for 1.0 hr and the reaction was concentrated to dryness. Benzene (100 mL) was added and the solution was evaporated to dryness again. The pale yellow solid was re-dissolved in methylene chloride (200 mL) and dripped, under argon, into a solution of 4-(4-amino-phenyl)-piperidine-1-carboxylic acid tert-butyl ester (10.8 g, 39.0 mmol), and triethylamine (10.2 g, 100 mmol) in methylene chloride (250 mL) over 30 min. The reaction was stirred at room temperature for 1 hr then concentrated and the residue was taken up in EtOAc (500 mL) and washed with hydrochloric acid (0.1N, 200 mL), water (200 mL), saturated sodium bicarbonate solution (200 mL), and brine (200 mL). The organic layer was dried with anhydrous sodium sulfate and filtered. The solvent was removed and the residue was triturated with hexanes to give 4-{4-[(2-phenyl-5-trifluoromethyl-oxazole-4-carbonyl)-amino]-phenyl}-piperidine-1-carboxylic acid tert-butyl ester as a pale yellow solid (19.24 g, 96% yield). ES-MS for $C_{27}H_{28}F_3N_3O_4$ calcd. (m/e) 515, observed 516 (M+H).

To a suspension of 4-{4-[(2-phenyl-5-trifluoromethyl-oxazole-4-carbonyl)-amino]-phenyl}-piperidine-1-carboxylic acid tert-butyl ester (19.2 g, 37.3 mmol) in dichloromethane (250 mL) was added trifluoroacetic acid (30 mL). The solution was stirred at room temperature for 3 hrs. Solvents were evaporated and the residue was diluted with ethyl acetate (600 mL). The mixture was neutralized with 1N sodium hydroxide solution (final PH >10). The organic layer was separated and washed with water and brine. After the evaporation of solvents, a pale yellow solid was obtained as 2-phenyl-5-trifluoromethyl-oxazole-4-carboxylic acid (4-piperidin-4-yl-phenyl)-amide (15.3 g, 99%). LC-MS calcd for $C_{22}H_{20}F_3N_3O_2$ (m/e) 415, obsd 416 (M+H).

5-Methyl-2-phenyl-oxazole-4-carboxylic acid (4-piperidin-4-yl-phenyl)-amide

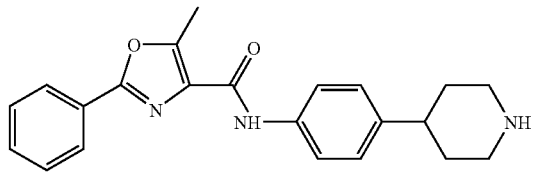

With a method similar to that used for the preparation of 2-phenyl-5-trifluoromethyl-oxazole-4-carboxylic acid (4-piperidin-4-yl-phenyl)-amide, 5-methyl-2-phenyl-oxazole-4-carboxylic acid (4-piperidin-4-yl-phenyl)-amide was prepared from 5-methyl-2-phenyl-oxazole-4-carboxylic acid and 4-(4-amino-phenyl)-piperidine-1-carboxylic acid tert-butyl ester. LC-MS calcd for $C_{22}H_{23}N_3O_2$ (m/e) 361, obsd 362 (M+H).

4-Phenyl-thiophene-2-carboxylic acid (4-piperidin-4-yl-phenyl)-amide

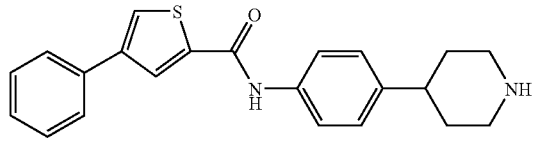

With a method similar to that used for the preparation of 2-phenyl-5-trifluoromethyl-oxazole-4-carboxylic acid (4-piperidin-4-yl-phenyl)-amide, 4-phenyl-thiophene-2-carboxylic acid (4-piperidin-4-yl-phenyl)-amide was prepared from 4-phenyl-thiophene-2-carboxylic acid and 4-(4-amino-phenyl)-piperidine-1-carboxylic acid tert-butyl ester. LC-MS calcd for $C_{22}H_{22}N_2OS$ (m/e) 362, obsd 363 (M+H).

2-Phenyl-5-trifluoroethyl-oxazole-4-carboxylic acid [4-((S)-pyrrolidin-3-yloxy)-phenyl]-amide hydrochloride

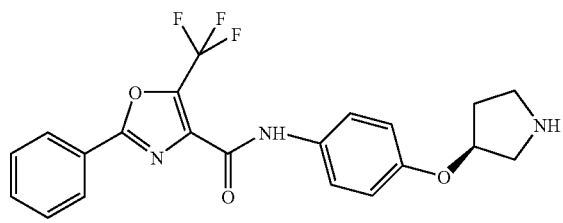

4-Fluoronitrobenzene (2.82 g, 20 mmol) was mixed with (S)-3-hydroxy-N-Boc-pyrrolidine (3.74 g, 20 mmol) in dry THF (100 mL). Sodium hydride (1.69 g, 60% in mineral oil) was added under ice bath and the mixture was stirred for 1 hr. The ice bath was removed and the mixture was stirred at room temperature overnight. Solvents were evaporated and the residue was extracted with ethyl acetate and 0.2N hydrochloric acid. The organic layer was washed with water and brine, dried over sodium sulfate. Solvents were evaporated and the residue was purified through ISCO column chromatography (silica gel, ethyl acetate in hexanes, 5% to 60% linear gradient). The desired fraction was concentrated and recrystallized from petroleum ether and ether (3:1 ratio) to give a pale yellow solid as (S)-3-(4-nitro-phenoxy)-pyrrolidine-1-carboxylic acid tert-butyl ester (4.33 g, 70.3% yield).

The above solid (3.08 g, 10 mmol) was dissolved into a mixture of THF and methanol (1/6 ratio) containing catalytic amount of palladium on carbon (10% Pd/C, 300 mg). The mixture was hydrogenated at 50 psi for 1.5 hr and filtered through a layer of celite. Solvents were evaporated to give an oil as (S)-3-(4-amino-phenoxy)-pyrrolidine-1-carboxylic acid tert-butyl ester (2.78 g, 100%).

2-Phenyl-5-trifluoromethyl-oxazole-4-carboxylic acid (2.57 g, 10 mmol) was suspended in dichloromethane (20 mL). Oxalyl chloride (2M in dichloromethane, 10 mL) was added followed by DMF (0.028 mL). The mixture was stirred for 1 hr and solvents were evaporated. The residue was treated with benzene (20 mL) and solvents were evaporated. The residue was dissolved in dichloromethane (30 mL) and treated with a mixture of (S)-3-(4-amino-phenoxy)-pyrrolidine-1-carboxylic acid tert-butyl ester (2.78 g, 10 mmol) and triethylamine (3.6 mL, 25 mmol) under ice bath. The mixture was stirred for 30 minutes and ice bath was removed. The solution was further stirred for 2 hrs. Solvents were evaporated and the residue was extracted with 0.1N hydrochloric acid and ethyl acetate. The organic layer was washed with water, concentrated sodium bicarbonate solution and brine. Solvents were evaporated and the residue was purified through ISCO column chromatography (silica gel, ethyl acetate in hexanes, 10% to 80% linear gradient) to give (S)-3-{4-[(2-phenyl-5-trifluoromethyl-oxazole-4-carbonyl)-amino]-phenoxy}-pyrrolidine-1-carboxylic acid tert-butyl ester (4.4 g, 85.1% yield). LC-MS for $C_{26}H_{26}F_3N_3O_5$ (m/e) calcd 517, obsd 516 (M−H).

The above (S)-3-{4-[(2-phenyl-5-trifluoromethyl-oxazole-4-carbonyl)-amino]-phenoxy}-pyrrolidine-1-carboxylic acid tert-butyl ester (4.4 g) was dissolved in dichloromethane (6 mL) and anhydrous hydrogen chloride in ether (3M, 12 mL) was added. The clear solution was kept at room temperature overnight. The white solid was filtered and washed with ether then dried under vacuum to give 2-phenyl-5-trifluoromethyl-oxazole-4-carboxylic acid [4-(S)-pyrrolidin-3-yloxy)-phenyl]-amide hydrochloride (4.0 g, 96% yield). LC-MS for $C_{21}H_{18}F_3N_3O_3$ (m/e) calcd 417, obsd 418 (M+H).

Preparation of 2-(2-chloro-phenyl)-5-trifluoromethyl-oxazole-4-carboxylic acid

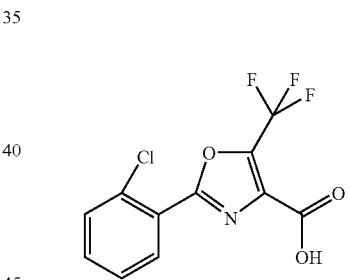

Amino-acetic acid methyl ester (5 g, 40 mmol) was suspended in DMF and treated with triethylamine (13.9 mL, 100 mmol) and 2-chloro-benzoyl chloride (5 mL, 40 mmol). The reaction mixture was stirred at room temperature overnight. Water was added to the reaction, and the mixture was extracted with ethyl acetate three times. The organic layers were combined and dried over sodium sulfate, filtered and concentrated. The residue was purified by flash chromatography using ethyl acetate/hexane to yield (2-chloro-benzoylamino)-acetic acid methyl ester as a light yellow solid. LCMS calcd for C10H10ClNO3 (m/e) 227, obsd 228 (M+H).

To a solution of above (2-chloro-benzoylamino)-acetic acid methyl ester (6 g, 26 mmol) in 30 mL of methanol, was added three equivalents of lithium hydroxide hydrate in 10 mL of water. The solution was stirred at room temperature for 1 hour, concentrated and mixed with water. Citric acid was added until pH of the solution was adjusted to pH 2-3. The mixture was extracted with ethyl acetate and the organic layer was washed with water and brine, dried over MgSO₄, filtered and concentrated to dryness to give (2-chloro-benzoylamino)-acetic acid as a solid. To a solution of (2-chlorobenzoylamino)-acetic acid in 40 mL of acetone at −20° C. was added excess of trifluoroacetic anhydride. The mixture was warmed up to room temperature and stirred overnight. The solvent was removed under vacuum. The residue was poured into 400 mL of water and stirred for 20 min. The solid was filtered out and washed with 2×100 mL of water, and dried under vacuum to give 2-(2-chloro-benzoylamino)-4,4,4-trifluoro-3,3-dihydroxy-butyric acid as a red solid. This red solid was suspended in 80 mL of methanol, and heated to reflux for 30 min. The solvent was removed and the mixture was purified by flash chromatography using ethyl acetate/hexane to give 2-(2-chloro-benzoylamino)-4,4,4-trifluoro-3,3-dihydroxy-butyric acid methyl ester as a light yellow solid. The methyl ester was suspended in 100 g of phosphorus oxychloride, and stirred at 80° C. overnight. The reaction mixture was concentrated to remove excess $POCl_3$. The remaining oil was diluted with toluene, and poured into a mixture of ice-water. The layers were separated and the organic layer was washed with water and diluted sodium bicarbonate and then concentrated to dryness. The solid was dissolved in 30 mL of methanol and treated with 2.5 equivalent of lithium hydroxide in 30 mL of water, and stirred for 30 min. Methanol was removed under vacuum, and the mixture was diluted with water. pH of the solution was adjusted to about 3 with 12 M hydrochloric acid, and the mixture was extracted with ethyl acetate. The organic layer was concentrated and purified by flash chromatography to give 1.67 g of 2-(2-chloro-phenyl)-5-trifluoromethyl-oxazole-4-carboxylic acid as a light yellow solid. LCMS calcd for C11H5ClF3NO3 (m/e) 291, obsd 292 (M+H).

Preparation of 2-(2-trifluoromethoxy-phenyl)-5-trifluoromethyl-oxazole-4-carboxylic acid

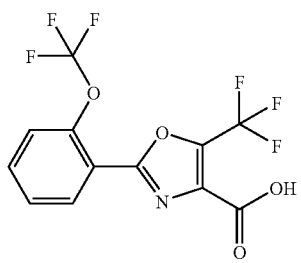

With a method similar to that used for the preparation of 2-(2-chloro-phenyl)-5-trifluoromethyl-oxazole-4-carboxylic acid above. 2-(2-trifluoromethoxy-phenyl)-5-trifluoromethyl-oxazole-4-carboxylic acid was prepared from 2-trifluoromethoxy-benzoyl chloride, amino-acetic acid methyl ester and trifluoroacetic anhydride. LCMS calcd for C12H5F6NO4 (m/e) 341, obsd 342 (M+H).

Preparation of 5-ethyl-2-phenyl-oxazole-4-carboxylic acid

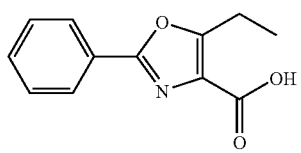

Lithium bis(trimethylsilyl)amide (1M in THF, 10.5 mL, 10.5 mmol) was added to N-(diphenylmethylene)glycine benzyl ester (3.28 g, 10 mmol) in tetrahydrofuran (10 mL) at −78° C. under argon. The reaction mixture was stirred at this temperature for about 1 hr. Propionyl chloride (0.913 mL, 10.5 mmol) in tetrahydrofuran (5 mL) was slowly added into the above mixture and stirred for 30 minutes. The reaction mixture was warmed up to room temperature and let stir overnight. After the completion of the above reaction, the reaction mixture was cooled to −40° C. quenched with 50 mL dilute hydrochloride acid (3N) and stirred at room temperature for 2 hr. After removal of tetrahydrofuran, the aqueous solution was extracted with ethyl acetate (3×50 mL), ether (1×50 mL) and $CH_2Cl_2$ (50 mL). The aqueous solution was concentrated in vacuo to about ½ volume and lyophilized to give 2-amino-4-methyl-3-oxo-butanoic acid benzyl ester hydrochloride salt, which was used in the next step without further purification.

Benzoyl chloride (0.875 mL, 7.46 mmol) was slowly added to a mixture of 2-amino-4-methyl-3-oxo-butanoic acid benzyl ester acid chloride (1.75 g, 6.789 mmol) and anhydrous pyridine (10 mL) in dichloromethane (50 mL) at ice bath temperature. The reaction mixture was stirred at room temperature for 1 hr, after which the solvent was removed and water was added. The resulted mixture was extracted with ethyl acetate. The organic layers were collected, washed with water (2×50 mL) brine (50 mL), dried over magnesium sulfate, and concentrate in vacuo. Flash chromatography (Merck silica gel 60, 230-400 mesh, 0-20% ethyl acetate in hexane for 30 min) gave 2-benzoylamino-4-methyl-3-oxo-butanoic acid benzyl ester (1.35 g). LCMS calcd for C19H19NO4 (m/e) 325, obsd 326 (M+H).

A mixture of 2-benzoylamino-4-methyl-3-oxo-butanoic acid benzyl ester (1.26 g, 3.88 mmol), triphenylphosphine (2.64 g, 10.09 mmol), and iodine (1.04 g, 8.225 mmol) in tetrahydrofuran (60 mL) was cooled to −78° C., followed by addition of triethylamine (2.18 mL, 15.52 mmol). The resulting solution was stirred at −78° C. for about 10 min, and then was warmed up to room temperature for about 1 hr. The solvent was removed and the residue was triturated with dichloromethane and filtered. The filtrate was evaporated and the residue dissolved in 70 mL of ethyl acetate, washed with 0.5 M citric acid (2×50 mL), saturated sodium bicarbonate (2×50 mL), and brine, dried over magnesium sulfate, filtered and then concentrated in vacuo. Flash chromatography (Merck silica gel 60, 230-400 mesh, 0-10% ethyl acetate in hexane) gave 5-ethyl-2-phenyl-oxazole-4-carboxylic acid benzyl ester (1 g) as a light yellow solid. LCMS calcd for C19H17NO3 (m/e) 321, obsd 322 (M+H).

A solution of 5-ethyl-2-phenyl-oxazole-4-carboxylic acid benzyl ester (1 g, 3.25 mmol) in 30 mL of ethanol was hydrogenated at 30 psi with 10% Pd/C (200 mg) at room temperature for two hours. The reaction mixture was filtered through a celite plug, evaporated and placed under high vacuum to give 5-ethyl-2-phenyl-oxazole-4-carboxylic acid, that was used without further purification. LCMS calcd for C12H11NO3 (m/e) 217, obsd 218 (M+H).

2-Phenyl-5-ethyl-oxazole-4-carboxylic acid (4-piperidin-4-yl-phenyl)-amide

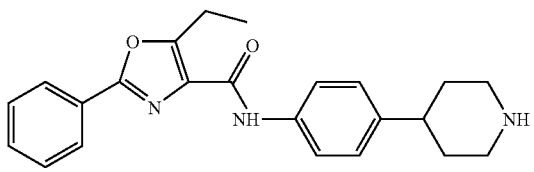

A mixture of 2-phenyl-5-ethyl-oxazole-4-carboxylic acid (180 mg, 0.829 mmol), 4-(4-amino-phenyl)-piperidine-1-carboxylic acid tert-butyl ester (218 mg, 0.79 mmol), triethylamine (467 mL, 3.316 mmol), and BOP (366 mg, 0.89 mmol) in 5 mL DMSO was stirred at room temperature for 1.0 hr. The reaction was taken up in EtOAc (50 mL) and washed with hydrochloric acid (0.1N, 20 mL), water (20 mL), saturated sodium bicarbonate solution (20 mL), and brine (20 mL). The organic layer was dried with anhydrous magnesium sulfate and filtered to give 4-{4-[(2-phenyl-5-ethyl-oxazole-4-carbonyl)-amino]-phenyl}-piperidine-1-carboxylic acid tert-butyl ester. ES-MS for $C_{28}H_{33}N_3O_4$ calcd. (m/e) 47.5, observed 476 (M–H).

To 4-{4-[(2-phenyl-5-ethyl-oxazole-4-carbonyl)-amino]-phenyl}-piperidine-1-carboxylic acid tert-butyl ester (330 mg, 0.694 mmol) was added 2N HCl in ethyl acetate (80 mL). The solution was stirred at room temperature for 1 hr. Solvents were evaporated and the residue was diluted with ethyl acetate (100 mL). The organic layer was washed with saturated sodium bicarbonate (3×) and dried over magnesium sulfate The solvent was evaporated to give 2-phenyl-5-ethyl-oxazole-4-carboxylic acid (4-piperidin-4-yl-phenyl)-amide (155 mg). LC-MS calcd for $C_{23}H_{25}N_3O_2$ (m/e) 375, obsd 376 (M+H).

Part II

Preparation of Preferred Compounds

Example 1

Preparation of 2-phenyl-5-trifluoromethyl-oxazole-4-carboxylic acid [4-(3-trifluoromethyl-phenyl)-3,4,5,6-tetrahydro-2H-[1,2']bipyridinyl-5'-yl]-amide

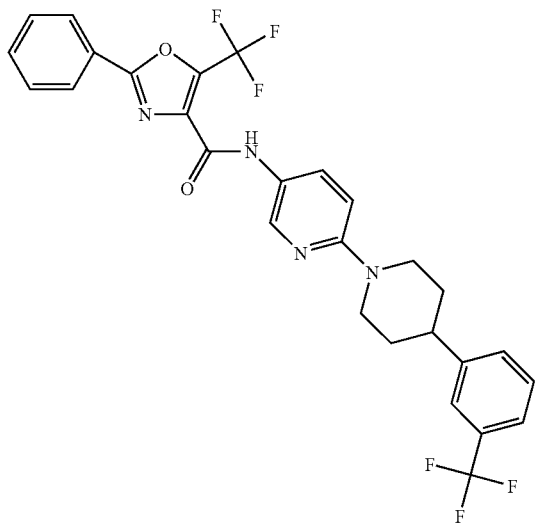

To a mixture of 2-phenyl-5-trifluoromethyl-oxazole-4-carboxylic acid (500 mg, 1.90 mmol) in methylene chloride (15 mL) was added oxalyl chloride (0.34 mL, 3.80 mmol) dropwise at 0° C. This was followed by a drop of DMF. The reaction was warmed to room temperature and stirred at room temperature for 1.5 hr. The mixture was concentrated to dryness to afford 2-phenyl-5-trifluoromethyl-oxazole-4-carbonyl chloride as a light yellow solid which was used in the next step without further purification.

To a solution of 4-(3-trifluoromethyl-phenyl)-3,4,5,6-tetrahydro-2H-[1,2']bipyridinyl-5'-ylamine (400 mg, 1.24 mmol) in methylene chloride (10 mL) was added diisopropylethylamine (0.60 mL, 3.30 mmol) followed by 2-phenyl-5-trifluoromethyl-oxazole-4-carbonyl chloride (300 mg, 1.10 mmol). The reaction was stirred at room temperature for 24 hours and then diluted with ethyl acetate. The organic layer was washed with saturated sodium bicarbonate, dried over magnesium sulfate, filtered and evaporated to dryness under vacuum. The residue was purified by HPLC to yield 2-phenyl-5-trifluoromethyl-oxazole-4-carboxylic acid [4-(3-trifluoromethyl-phenyl)-3,4,5,6-tetrahydro-2H-[1,2']bipyridinyl-5'-yl]-amide as a light purple solid. The NMR spectrum obtained on the sample is compatible with its structure. LCMS calcd for C28H22F6N4O2 (m/e) 560, obsd 561 (M+H).

Example 2

Preparation of 4-(4-{5-[(2-phenyl-5-trifluoromethyl-oxazole-4-carbonyl)-amino]-pyridin-2-yl}-piperazin-1-yl)-benzoic acid ethyl ester

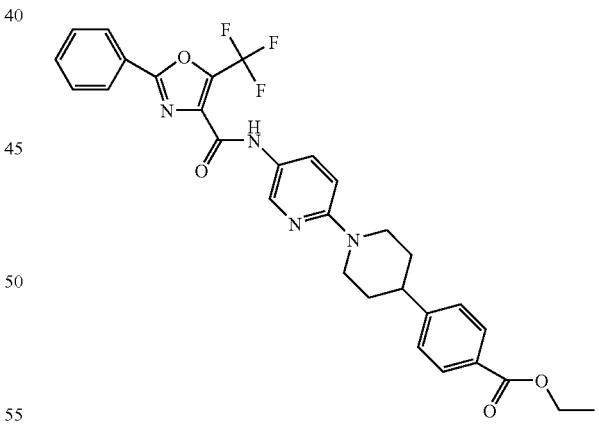

With a method similar to that used for the preparation of 2-phenyl-5-trifluoromethyl-oxazole-4-carboxylic acid [4-(3-trifluoromethyl-phenyl)-3,4,5,6-tetrahydro-2H-[1,2']bipyridinyl 5'-yl]-amide above, 4-(4-{5-[(2-phenyl-5-trifluoromethyl-oxazole-4-carbonyl)-amino]-pyridin-2-yl}-piperazin-1-yl)-benzoic acid ethyl ester was prepared from 2-phenyl-5-trifluoromethyl-oxazole-4-carbonyl chloride and 4-[4-(5-amino-pyridin-2-yl)-piperazin-1-yl]-benzoic acid ethyl ester. LCMS calcd for C29H26F3N5O4 (m/e) 565, obsd 566 (M+H).

Example 3

Preparation of 2-phenyl-5-trifluoromethyl-oxazole-4-carboxylic acid [6-(4-pyrimidin-2-yl-piperazin-1-yl)-pyridin-3-yl]-amide

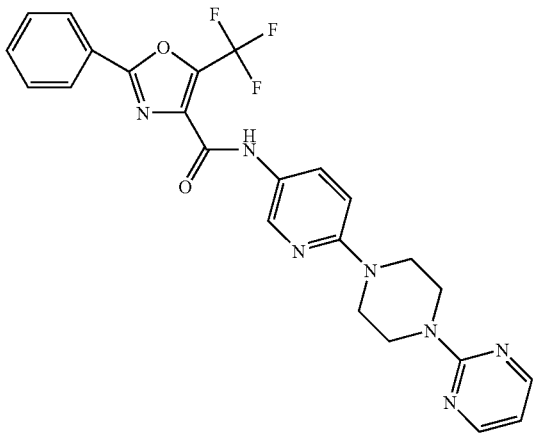

To a solution of 2-phenyl-5-trifluoromethyl-oxazole-4-carboxylic acid (100 mg, 0.39 mmol) in methylene chloride (15 mL) was added 6-(4-pyrimidin-2-yl-piperazin-1-yl)-pyridin-3-ylamine (100 mg, 0.39 mmol) and diisopropylethylamine (0.35 mL, 1.90 mmol). To this solution was added bromo-tris-pyrrolidino-phosphoniumhexafluorophosphate (PyBrOP) in one portion (280 mg, 0.59 mmol). The mixture was stirred at room temperature overnight. The residue was purified by HPLC to yield 2-phenyl-5-trifluoromethyl-oxazole-4-carboxylic acid [6-(4-pyrimidin-2-yl-piperazin-1-yl)-pyridin-3-yl]-amide as a light yellow powder. The NMR spectrum obtained on the sample is compatible with its structure. LCMS calcd for C24H20F3N7O2 (m/e) 495, obsd 496 (M+H).

Example 4

Preparation of 4-(4-{5-[(1-pyridin-2-yl-3-trifluoromethyl-1H-pyrazole-4-carbonyl)-amino]-pyridin-2-yl}-piperazin-1-yl)-benzoic acid ethyl ester

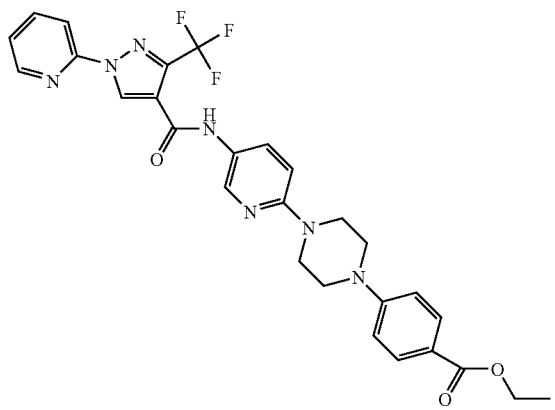

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 4-(4-{5-[(1-pyridin-2-yl-3-trifluoromethyl-1H-pyrazole-4-carbonyl)-amino]-pyridin-2-yl}-piperazin-1-yl)-benzoic acid ethyl ester was prepared from 1-pyridin-2-yl-3-trifluoromethyl-1H-pyrazole-4-carboxylic acid and 4-[4-(5-amino-pyridin-2-yl)-piperazin-1-yl]-benzoic acid ethyl ester. LCMS calcd for C28H26F3N7O3 (m/e) 565, obsd 566 (M+H).

Example 5

Preparation of 2-phenyl-5-trifluoromethyl-oxazole-4-carboxylic acid [6-[4-(4-trifluoromethyl-phenyl)-piperazin-1-yl]-pyridin-3-yl]-amide

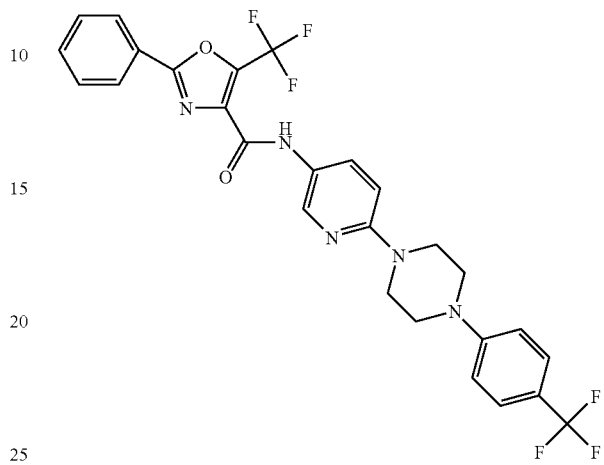

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid {6-[4-(4-trifluoromethyl-phenyl)-piperazin-1-yl]-pyridin-3-yl}-amide was prepared from 2-phenyl-5-trifluoromethyl-oxazole-4-carboxylic acid and 6-[4-(4-trifluoromethyl-phenyl)-piperazin-1-yl]-pyridin-3-ylamine. LCMS calcd for C27H21F6N5O2 (m/e) 561, obsd 562 (M+H).

Example 6

Preparation of 2-phenyl-5-trifluoromethyl-oxazole-4-carboxylic acid {6-[4-(4-methoxy-phenyl)-piperazin-1-yl]-pyridin-3-yl}-amide

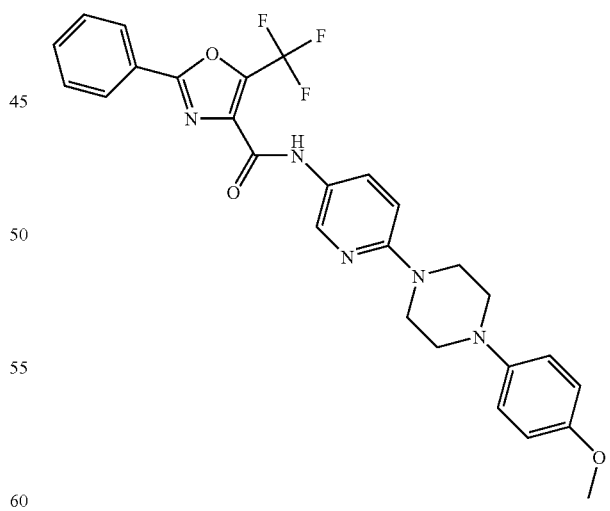

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid {6-[4-(4-methoxy-phenyl)-piperazin-1-yl]-pyridin-3-yl}-amide was prepared from 2-phenyl-5-trifluoromethyl-oxazole-4- carboxylic acid and 6-[4-(4-methoxy-phenyl)-piperazin-1-yl]-pyridin-3-ylamine. LCMS calcd for C27H24F3N5O3 (m/e) 523, obsd 524 (M+H).

Example 7

Preparation of 2-phenyl-5-trifluoromethyl-oxazole-4-carboxylic acid {6-[4-(2-trifluoromethyl-phenyl)-piperazin-1-yl]-pyridin-3-yl}-amide

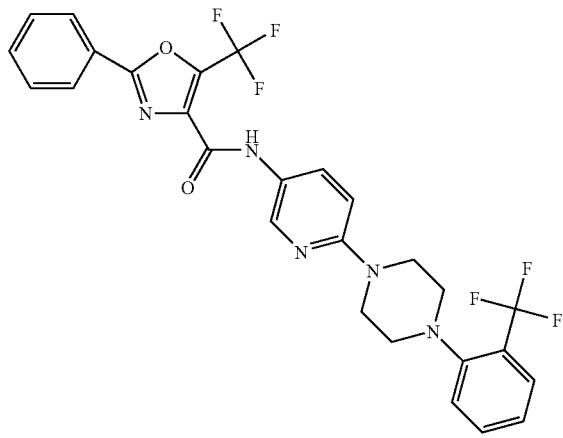

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid {6-[4-(2-trifluoromethyl-phenyl)-piperazin-1-yl]-pyridin-3-yl}-amide was prepared from 2-phenyl-5-trifluoromethyl-oxazole-4-carboxylic acid and 6-[4-(2-trifluoromethyl-phenyl)-piperazin-1-yl]-pyridin-3-ylamine. LCMS calcd for C27H21F6N5O2 (m/e) 561, obsd 562 (M+H).

Example 8

Preparation of 2-phenyl-5-trifluoromethyl-oxazole-4-carboxylic acid {6-[4-(3-trifluoromethyl-phenyl)-piperazin-1-yl]-pyridin-3-yl}-amide

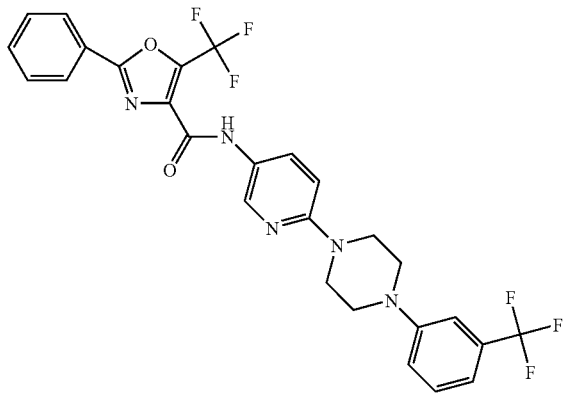

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid {6-[4-(3-trifluoromethyl-phenyl)-piperazin-1-yl]-pyridin-3-yl}-amide was prepared from 2-phenyl-5-trifluoromethyl-oxazole-4-carboxylic acid and 6-[4-(3-trifluoromethyl-phenyl)-piperazin-1-yl]-pyridin-3-ylamine. LCMS calcd for C27H21F6N5O2 (m/e) 561, obsd 562 (M+H).

Example 9

Preparation of 2-phenyl-5-trifluoromethyl-oxazole-4-carboxylic acid {6-[4-(2-methoxy-phenyl)-piperazin-1-yl]pyridin-3-yl}-amide

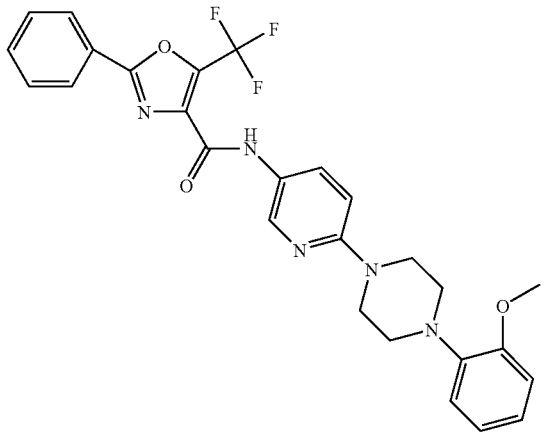

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid {6-[4-(2-methoxy-phenyl)-piperazin-1-yl]-pyridin-3-yl}-amide was prepared from 2-phenyl-5-trifluoromethyl-oxazole-4-carboxylic acid and 6-[4-(2-methoxy-phenyl)-piperazin-1-yl]-pyridin-3-ylamine. LCMS calcd for C27H24F3N5O3 (m/e) 523, obsd 524 (M+H).

Example 10

Preparation of 2-phenyl-5-trifluoromethyl-oxazole-4-carboxylic acid {6-[4-(3-methoxy-phenyl)-piperazin-1-yl]-pyridin-3-yl}-amide

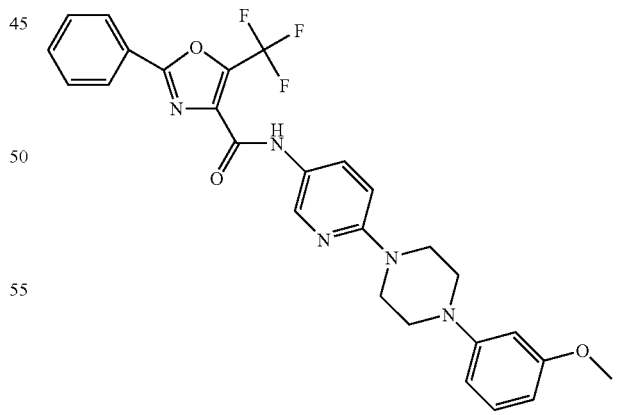

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid {6-[4-(3-methoxy-phenyl)-piperazin-1-yl]-pyridin-3-yl}-amide was prepared from 2-phenyl-5-trifluoromethyl-oxazole-4- carboxylic acid and 6-[4-(3-methoxy-phenyl)-piperazin-1-yl]-pyridin-3-ylamine. LCMS calcd for C27H24F3N5O3 (m/e) 523, obsd 524 (M+H).

Example 11

Preparation of 2-phenyl-5-trifluoromethyl-oxazole-4-carboxylic acid [4-hydroxy-4-(3-trifluoromethyl-phenyl)-3,4,5,6-tetrahydro-2H-[1,2']bipyridinyl-5'-yl]-amide

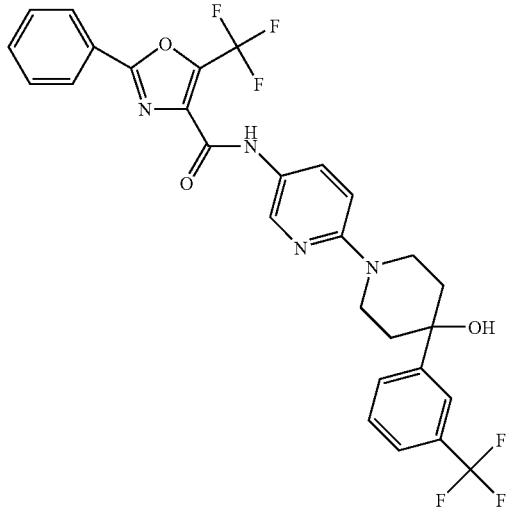

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid [4-hydroxy-4-(3-trifluoromethyl-phenyl)-3,4,5,6-tetrahydro-2H-[1,2']bipyridinyl-5'-yl]-amide was prepared from 2-phenyl-5-trifluoromethyl-oxazole-4-carboxylic acid and 5'-amino-4-(3-trifluoromethyl-phenyl)-3,4,5,6-tetrahydro-2H-[1,2']bipyridinyl-4-ol. LCMS calcd for C28H22F6N4O3 (m/e) 576, obsd 577 (M+H).

Example 12

Preparation of 2-phenyl-5-trifluoromethyl-oxazole-4-carboxylic acid [6-(4-phenyl-piperazin-1-yl)-pyridin-3-yl]-amide

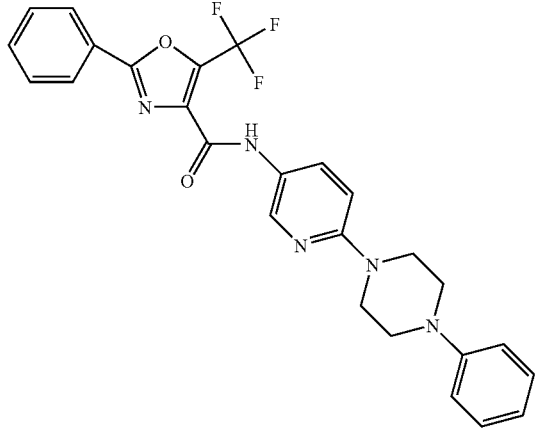

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid [6-(4-phenyl-piperazin-1-yl)-pyridin-3-yl]-amide was prepared from 2-phenyl-5-trifluoromethyl-oxazole-4-carboxylic acid and 6-(4-phenyl-piperazin-1-yl)-pyridin-3-ylamine. LCMS calcd for C26H22F3N5O2 (m/e) 493, obsd 494 (M+H).

Example 13

Preparation of 2-phenyl-5-trifluoromethyl-oxazole-4-carboxylic acid (4-phenyl-3,4,5,6-tetrahydro-2H-[1,2']bipyridinyl-5'-yl)-amide

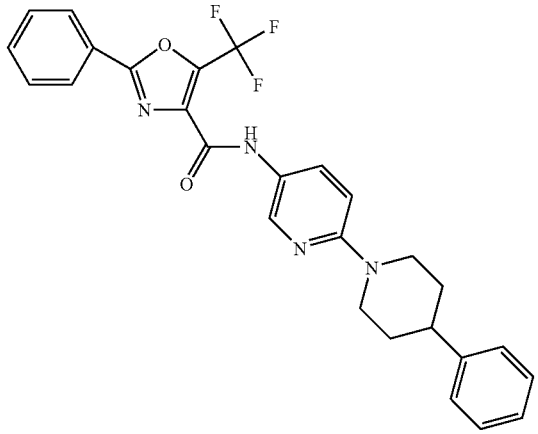

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid (4-phenyl-3,4,5,6-tetrahydro-2H-[1,2']bipyridinyl-5'-yl)-amide was prepared from 2-phenyl-5-trifluoromethyl-oxazole-4-carboxylic acid and 4-phenyl-3,4,5,6-tetrahydro-2H-[1,2']bipyridinyl-5'-ylamine. LCMS calcd for C27H23F3N4O2 (m/e) 492, obsd 493 (M+H).

Example 14

Preparation of 2-phenyl-5-trifluoromethyl-oxazole-4-carboxylic acid (4-hydroxy-4-phenyl-3,4,5,6-tetrahydro-2H-[1,2']bipyridinyl-5'-yl)-amide

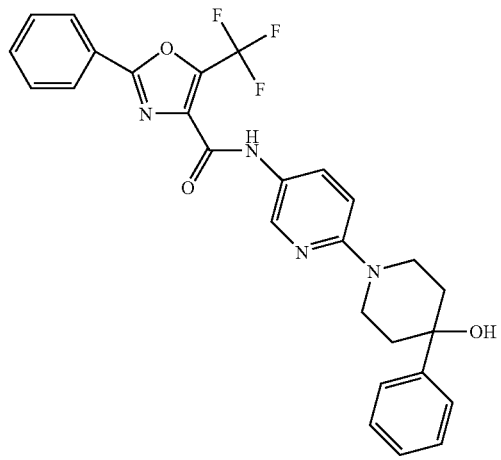

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 2-phenyl-5-trifluoromethyl-oxazole-4-carboxylic acid (4-hydroxy-4-phenyl-3,4,5,6-tetrahydro-2H-[1,2']bipyridinyl-5'-yl)-amide was prepared from 2-phenyl-5-trifluoromethyl-oxazole-4-carboxylic acid and 5'-amino-4-phenyl-3,4, 5,6-tetrahydro-2H-[1,2']bipyridinyl-4-ol. LCMS calcd for C27H23F3N4O3 (m/e) 508, obsd 509 (M+H).

Example 15

Preparation of 1-pyridin-2-yl-3-trifluoromethyl-1H-pyrazole-4-carboxylic acid [4-(3-trifluoromethyl-phenyl)-3,4,5,6-tetrahydro-2H-[1,2']bipyridinyl-5'-yl]-amide

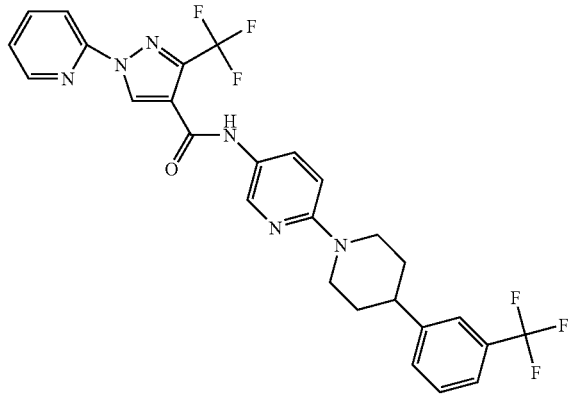

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 1-pyridin-2-yl-3-trifluoromethyl-1H-pyrazole-4-carboxylic acid [4-(3-trifluoromethyl-phenyl)-3,4,5,6-tetrahydro-2H-[1,2']bipyridinyl-5'-yl]-amide was prepared from 1-pyridin-2-yl-3-trifluoromethyl-1H-pyrazole-4-carboxylic acid and 4-(3-trifluoromethyl-phenyl)-3,4,5,6-tetrahydro-2H-[1,2'] bipyridinyl-5'-ylamine. LCMS calcd for C27H22F6N6O (m/e) 560, obsd 561 (M+H).

Example 16

Preparation of 1-pyridin-2-yl-3-trifluoromethyl-1H-pyrazole-4-carboxylic acid {6-[6-(4-(4-fluoro-phenyl)-piperazin-1-yl]-pyridin-3-yl}-amide

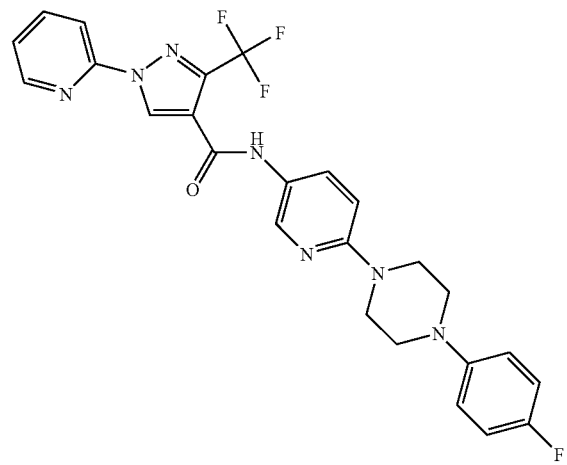

With a method similar to that used for the preparation of 2-phenyl-5-trifluoromethyl-oxazole-4-carboxylic acid [6-(4-pyrimidin-2-yl-piperazin-1-yl)-pyridin-3-yl]-amide above, 1-pyridin-2-yl-3-trifluoromethyl-1H-pyrazole-4-carboxylic acid {6-[4-(4-fluoro-phenyl)-piperazin-1-yl]-pyridin-3-yl}-amide was prepared from 1-pyridin-2-yl-3-trifluoromethyl-1H-pyrazole-4-carboxylic acid and 6-[4-(4-fluoro-phenyl)-piperazin-1-yl]-pyridin-3-ylamine. LCMS calcd for C25H21F4N7O (talc) 511, obsd 512 (M+H).

Example 17

Preparation of 4-(4-{5-[(2-phenyl-5-trifluoromethyl-oxazole-4-carbonyl)-amino]-pyridin-2-yl}-piperazin-1-yl)-benzoic acid

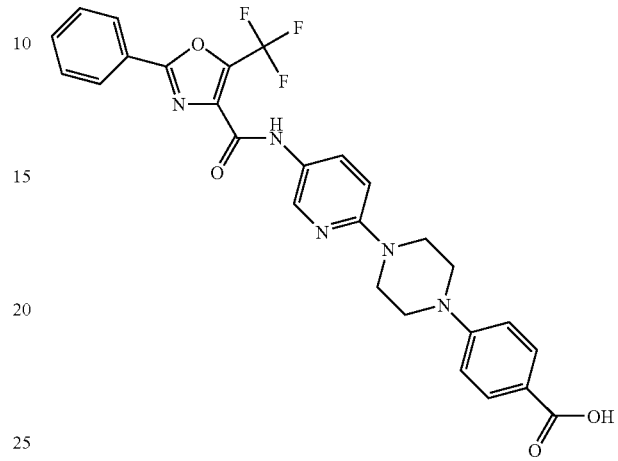

To 4-(4-{5-[(2-phenyl-5-trifluoromethyl-oxazole-4-carbonyl)-amino]-pyridin-2-yl}-piperazin-1-yl)-benzoic acid ethyl ester (130 mg, 0.23 mmol) dissolved in a 1:1 mixture of THF/methanol (2 mL) was added 1N LiOH (2.60 mL, 2.60 mmol). The mixture was stirred at rt overnight. The crude mixture was acidified to pH=1 and purified by HPLC to give 4-(4-{5-[(2-phenyl-5-trifluoromethyl-oxazole-4-carbonyl)-amino]-pyridin-2-yl}-piperazin-1-yl)-benzoic acid. The NMR spectrum obtained on the sample is compatible with its structure. LCMS calcd for C27H22F3N5O4 (m/e) 537, obsd 538 (M+H).

Example 18

Preparation of 3-(4-{5-[(2-phenyl-5-trifluoromethyl-oxazole-4-carbonyl)-amino]-pyridin-2-yl}-piperazin-1-yl)-benzoic acid

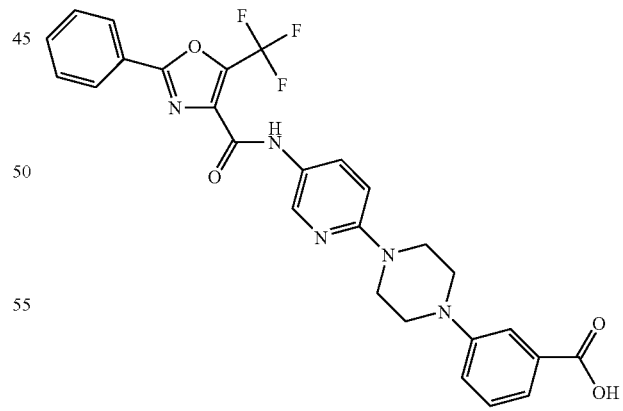

With a method similar to that used for the preparation of 4-(4-{5-[(2-phenyl-5-trifluoromethyl-oxazole-4-carbonyl)-amino]-pyridin-2-yl}-piperazin-1-yl)-benzoic acid above, 3-(4-{5-[(2-phenyl-5-trifluoromethyl-oxazole-4-carbonyl)-amino]-pyridin-2-yl}-piperazin-1-yl)-benzoic acid was prepared from 2-phenyl-5-trifluoromethyl-oxazole-4-carboxylic acid and 3-[4-(5-amino-pyridin-2-yl)-piperazin-1-yl]- benzoic acid ethyl ester followed by ester hydrolysis. LCMS calcd for C27H22F3N5O4 (m/e) 537, obsd 538 (M+H).

Example 19

Preparation of 2-(4-{5-[(2-phenyl-5-trifluoromethyl-oxazole-4-carbonyl)-amino]-pyridin-2-yl}-piperazin-1-yl)-benzoic acid

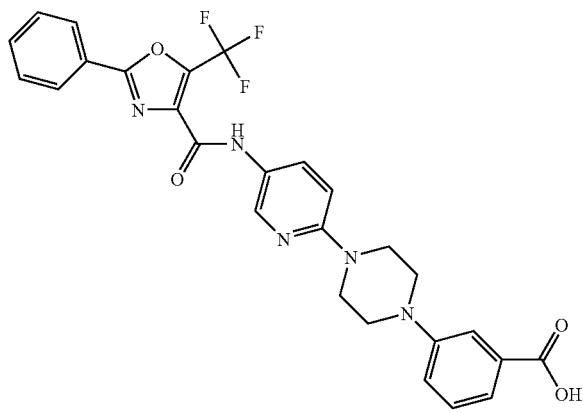

With a method similar to that used for the preparation of 4-(4-{5-[(2-phenyl-5-trifluoromethyl-oxazole-4-carbonyl)-amino]-pyridin-2-yl}-piperazin-1-yl)-benzoic acid above, 2-(4-{5-[(2-phenyl-5-trifluoromethyl-oxazole-4-carbonyl)-amino]-pyridin-2-yl}-piperazin-1-yl)-benzoic acid was prepared from 2-phenyl-5-trifluoromethyl-oxazole-4-carboxylic acid and 2-[4-(5-amino-pyridin-2-yl)-piperazin-1-yl]-benzoic acid methyl ester followed by ester hydrolysis. LCMS calcd for C27H22F3N5O4 (m/e) 537, obsd 538 (M+H).

Example 20

Preparation of 2-Phenyl-5-trifluoromethyl-oxazole-4-carboxylic acid {4-[4-(3-isopropyl-[1,2,4]oxadiazol-5-yl)-piperidin-1-yl]-phenyl}-amide

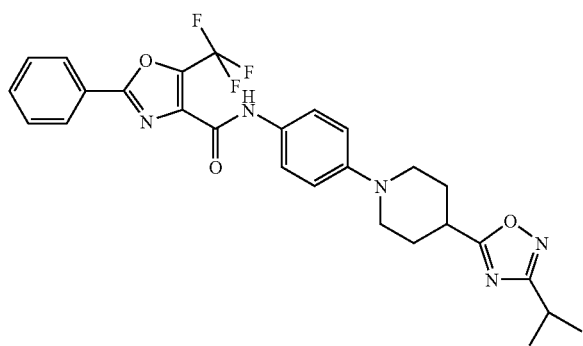

To a mixture of 1-{4-[(2-phenyl-5-trifluoromethyl-oxazole-4-carbonyl)-amino]-phenyl}-piperidine-4-carboxylic acid (200 mg, 0.435 mmol) in 2 mL of CH$_2$Cl$_2$ was added a drop of DMF and approximately 2 mL of oxalyl chloride dropwise (gas evolution observed). The resulting mixture was stirred at room temperature for 72 hours, then concentrated to produce a solid, which was triturated with ether, then suspended in 5 mL of THF. To this suspension was added triethylamine (110 mg, 151 µL, 1.088 mmol), followed by N-hydroxy-isobutyramidine (54 mg, 0.529 mmol). The resulting reaction mixture was stirred at room temperature overnight, then diluted with EtOAc, and washed twice with saturated NH$_4$Cl solution. The organic phase was then dried over Na$_2$SO$_4$, filtered, and concentrated. The residue was re-dissolved in 5 mL of THF, and treated with 4 N TBAF solution in THF (excess, ca. 2 mL). The mixture was stirred at room temperature overnight, and then diluted with EtOAc. The organic phase was washed with water, dried over Na$_2$SO$_4$, filtered, and concentrated. The crude product was purified by chromatography on silica gel (gradient elution with 10-50% ethyl acetate in hexanes) to produce 2-phenyl-5-trifluoromethyl-oxazole-4-carboxylic acid {4-[4-(3-isopropyl-[1,2,4]oxadiazol-5-yl)-piperidin-1-yl]-phenyl}-amide as an off-white solid. HRMS calcd for C27H26F3N5O3 (M+H) 526.2061, obsd 526.2059.

Example 21

Preparation of 2-phenyl-5-trifluoromethyl-oxazole-4-carboxylic acid {2-[4-(3-isopropyl-[1,2,4]oxadiazol-5-yl)-piperidin-1-yl]-pyrimidin-5-yl}-amide

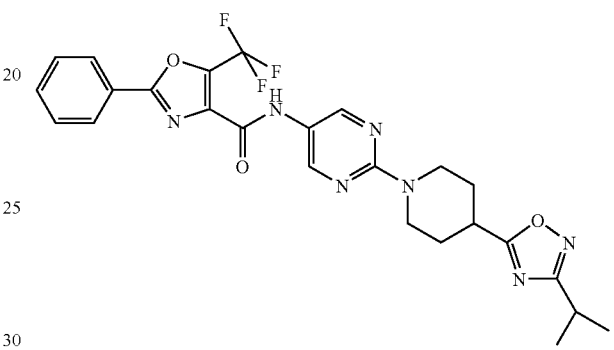

With a similar method to that used for the preparation of 2-phenyl-5-trifluoromethyl-oxazole-4-carboxylic acid {4-[4-(3-isopropyl-[1,2,4]oxadiazol-5-yl)-piperidin-1-yl]-phenyl}-amide above, 2-phenyl-5-trifluoromethyl-oxazole-4-carboxylic acid {2-[4-(3-isopropyl-[1,2,4]oxadiazol-5-yl)-piperidin-1-yl]-pyrimidin-5-yl}-amide was prepared from 1-{5-[(2-phenyl-5-trifluoromethyl-oxazole-4-carbonyl)-amino]-pyrimidin-2-yl}-piperidine-4-carboxylic acid and N-hydroxy-isobutyramidine. HRMS calcd for C25H24F3N7O3 (M+H) 528.1966, obsd 528.1964.

Example 22

Preparation of 2-phenyl-5-trifluoromethyl-oxazole-4-carboxylic acid [4-(3-isopropyl-[1,2,4]oxadiazol-5-yl)-3,4,5,6-tetrahydro-2H-[1,2']bipyridinyl-5'-yl]-amide

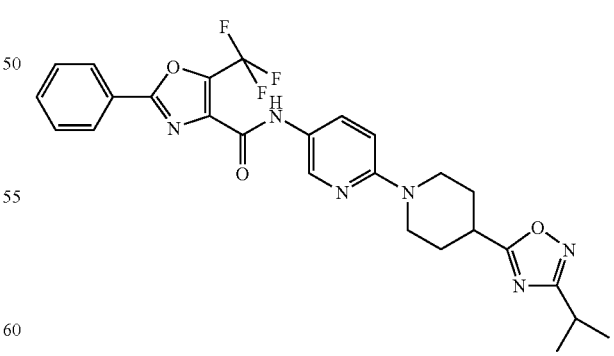

With a similar method to that used for the preparation of 2-phenyl-5-trifluoromethyl-oxazole-4-carboxylic acid {4-[4-(3-isopropyl-[1,2,4]oxadiazol-5-yl)-piperidin-1-yl]-phenyl}-amide above, 2-phenyl-5-trifluoromethyl-oxazole-4-carboxylic acid [4-(3-isopropyl-[1,2,4]oxadiazol-5-yl)-3,4, 5,6-tetrahydro-2H-[1,2']bipyridinyl-5'-yl]-amide was prepared from 5'-[(2-phenyl-5-trifluoromethyl-oxazole-4-carbonyl)-amino]-3,4,5,6-tetrahydro-2H-[1,2']bipyridinyl-4-carboxylic acid and N-hydroxy-isobutyramidine. HRMS calcd for C26H25F3N6O3 (M+H) 527.2013, obsd 527.2010.

Example 23

Preparation of 2-phenyl-5-trifluoromethyl-oxazole-4-carboxylic acid [4-(3-methyl-[1,2,4]oxadiazol-5-yl)-3,4,5,6-tetrahydro-2H-[1,2']bipyridinyl-5'-yl]-amide

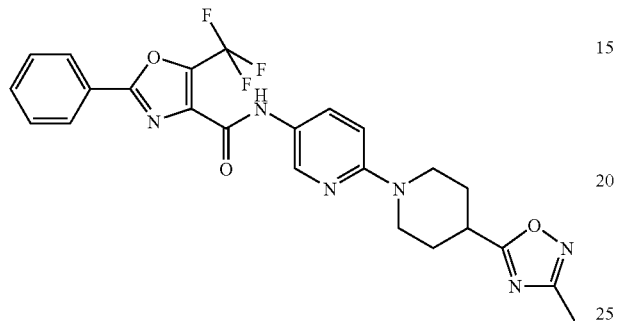

With a similar method to that used for the preparation of 2-phenyl-5-trifluoromethyl-oxazole-4-carboxylic acid {4-[4-(3-isopropyl-[1,2,4]oxadiazol-5-yl)-piperidin-1-yl]-phenyl}-amide above, 2-phenyl-5-trifluoromethyl-oxazole-4-carboxylic acid [4-(3-methyl-[1,2,4]oxadiazol-5-yl)-3,4,5,6-tetrahydro-2H-[1,2']bipyridinyl-5'-yl]-amide was prepared from 5'-[(2-phenyl-5-trifluoromethyl-oxazole-4-carbonyl)-amino]-3,4,5,6-tetrahydro-2H-[1,2']bipyridinyl-4-carboxylic acid and N-hydroxy-acetamidine. HRMS calcd for C24H21F3N6O3 (M+H) 499.1700, obsd 499.1698.

Example 24

Preparation of 2-phenyl-5-trifluoromethyl-oxazole-4-carboxylic acid [4-(3-cyclopropyl-[1,2,4]oxadiazol-5-yl)-3,4,5,6-tetrahydro-2H-[1,2']bipyridinyl-5'-yl]-amide

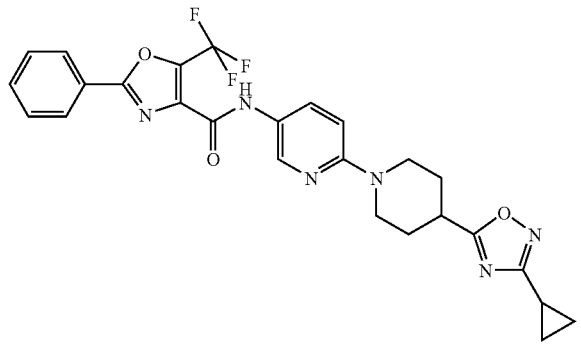

With a similar method to that used for the preparation of 2-phenyl-5-trifluoromethyl-oxazole-4-carboxylic acid {4-[4-(3-isopropyl-[1,2,4]oxadiazol-5-yl)-piperidin-1-yl]-phenyl}-amide above, 2-phenyl-5-trifluoromethyl-oxazole-4-carboxylic acid [4-(3-cyclopropyl-[1,2,4]oxadiazol-5-yl)-3,4,5,6-tetrahydro-2H-[1,2']bipyridinyl-5'-yl]-amide was prepared from 5'-[(2-phenyl-5-trifluoromethyl-oxazole-4-carbonyl)-amino]-3,4,5,6-tetrahydro-2H-[1,2']bipyridinyl-4-carboxylic acid and N-hydroxy-cyclopropanecarboxamidine. HRMS calcd for C26H23F3N6O3 (M+H) 525.1857, obsd 525.1855.

Example 25

Preparation of 2-phenyl-5-trifluoromethyl-oxazole-4-carboxylic acid {6-[3-(3-isopropyl-[1,2,4]oxadiazol-5-yl)-pyrrolidin-1-yl]-pyridin-3-yl}-amide

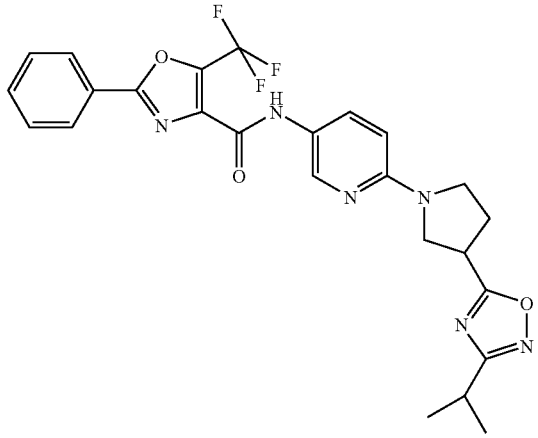

With a similar method to that used for the preparation of 2-phenyl-5-trifluoromethyl-oxazole-4-carboxylic acid {4-[4-(3-isopropyl-[1,2,4]oxadiazol-5-yl)-piperidin-1-yl]-phenyl}-amide above, 2-phenyl-5-trifluoromethyl-oxazole-4-carboxylic acid {6-[3-(3-isopropyl-[1,2,4]oxadiazol-5-yl)-pyrrolidin-1-yl]-pyridin-3-yl}-amide was prepared from 1-{5-[(2-phenyl-5-trifluoromethyl-oxazole-4-carbonyl)-amino]-pyridin-2-yl}-pyrrolidine-3-carboxylic acid and N-hydroxy-isobutyramidine. HRMS calcd for C25H23F3N6O3 (M+H) 513.1857, obsd 513.1855.

Example 26

Preparation of 2-(2-trifluoromethoxy-phenyl)-5-trifluoromethyl-oxazole-4-carboxylic acid [4-(3-isopropyl-[1,2,4]oxadiazol-5-yl)-3,4,5,6-tetrahydro-2H-[1,2]bipyridinyl-5'-yl]-amide

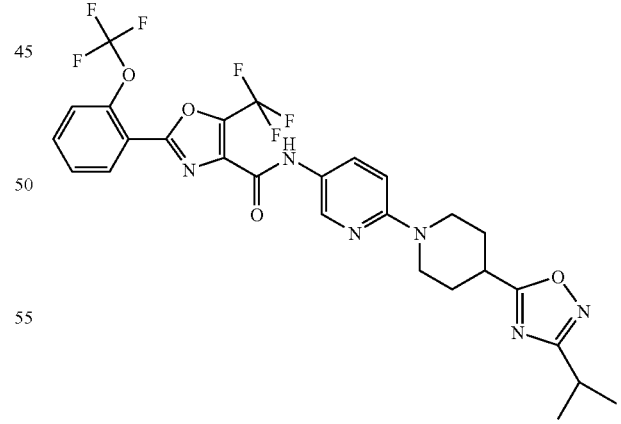

With a similar method to that used for the preparation of 2-phenyl-5-trifluoromethyl-oxazole-4-carboxylic acid {4-[4-(3-isopropyl-[1,2,4]oxadiazol-5-yl)-piperidin-1-yl]-phenyl}-amide above, 2-(2-trifluoromethoxy-phenyl)-5-trifluoromethyl-oxazole-4-carboxylic acid [4-(3-isopropyl-[1,2,4]oxadiazol-5-yl)-3,4,5,6-tetrahydro-2H-[1,2']bipyridinyl-5'-yl]-amide was prepared from 5'-{[2-(2-trifluoromethoxyphenyl)-5-trifluoromethyl-oxazole-4-carbonyl]-amino}-3,4,5,6-tetrahydro-2H-[1,2']bipyridinyl-4-carboxylic acid and N-hydroxy-isobutyramidine. HRMS calcd for C27H24F6N6O4 (M+H) 611.1836, obsd 611.1837.

Example 27

Preparation of 4-{4-[(2-phenyl-5-trifluoromethyl-oxazole-4-carbonyl)-amino]-phenyl}-3,4,5,6-tetrahydro-2H-[1,2']bipyridinyl-5'-carboxylic acid

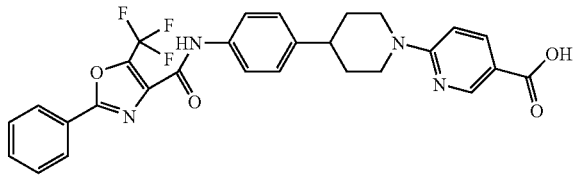

A mixture of 2-phenyl-5-trifluoromethyl-oxazole-4-carboxylic acid (4-piperidin-4-yl-phenyl)-amide (208 mg, 0.5 mmol) and 6-fluoronicotinic acid (72 mg, 0.5 mmol) in DMSO (2 L) containing potassium carbonate (135 mg, 1 mmol) was heated in a microwave at 135° C. for 35 minutes. The mixture was extracted with ethyl acetate and 0.1N hydrochloric acid. The organic layer was washed with water and brine. Solvents were evaporated and the residue was purified through ISCO column chromatography (silica gel, ethyl acetate in hexanes, 10% to 100% linear gradient). The collected fractions were concentrated and the white crystalline material was filtered to give 4-{4-[(2-phenyl-5-trifluoromethyl-oxazole-4-carbonyl)-amino]-phenyl}-3,4,5,6-tetrahydro-2H-[1,2']bipyridinyl-5'-carboxylic acid (40.5 mg). LC-MS for $C_{28}H_{23}F_3N_4O_4$ (m/e) calcd 536, obsd 537 (M+H). $^1$H-NMR is consistent with the desired structure.

Example 28

Preparation of 4-{4-[(4-phenyl-thiophene-2-carbonyl)-amino]-phenyl}-3,4,5,6-tetrahydro-2H-[1,2']bipyridinyl-5'-carboxylic acid

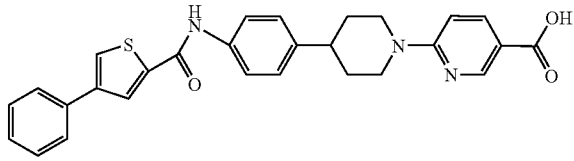

A mixture of 4-phenyl-thiophene-2-carboxylic acid (4-piperidin-4-yl-phenyl)-amide (181 mg, 0.5 mmol) and 6-fluoronicotinic acid (141 mg, 1 mmol) in dioxane (3 mL) containing diisopropylethylamine (0.5 mL, 2.7 mmol) was heated in a microwave at 175° C. for 30 minutes. The mixture was evaporated and extracted with ethyl acetate (containing THF and methanol) and 0.2N hydrochloric acid. The organic layer was dried and evaporated. The residue was crystallized from methanol and ethyl acetate to give a pale yellow solid as 4-{4-[(4-phenyl-thiophene-2-carbonyl)-amino]-phenyl}-3,4,5,6-tetrahydro-2H-[1,2']bipyridinyl-5'-carboxylic acid (114 mg). LC-MS for $C_{28}H_{25}N_3O_3S$ (m/e) calcd 483, obsd 484 (M+H). $^1$H-NMR is consistent with the desired structure.

Example 29

Preparation of 4-{4-[(5-methyl-2-phenyl-oxazole-4-carbonyl)-amino]-phenyl}-3,4,5,6-tetrahydro-2H-[1,2']bipyridinyl-5'-carboxylic acid

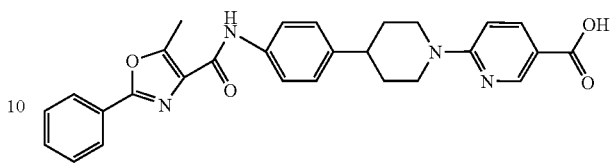

A mixture of 5-methyl-2-phenyl-oxazole-4-carboxylic acid (4-piperidin-4-yl-phenyl)-amide (181 mg, 0.5 mmol) and 6-fluoronicotinic acid (113 mg, 0.8 mmol) in dioxane (2 mL) containing diisopropylethylamine (0.5 mL, 2.7 mmol) was heated in a microwave at 175° C. for 30 minutes. The mixture was evaporated and extracted with ethyl acetate and aqueous citric acid solution. The organic layer was dried over sodium sulfate and solvents were evaporated. The residue was triturated with ethyl acetate and filtered to give a pale pink solid as 4-{4-[(5-methyl-2-phenyl-oxazole-4-carbonyl)-amino]-phenyl}-3,4,5,6-tetrahydro-2H-[1,2']bipyridinyl-5'-carboxylic acid (122.5 mg). LC-MS for $C_{28}H_{26}N_4O_4$ (m/e) calcd 482, obsd 483 (M+H). $^1$H-NMR is consistent with the desired structure.

Example 30

Preparation of 4-((S)-3-{4-[(2-phenyl-5-trifluoromethyl-oxazole-4-carbonyl)-amino]-phenoxy}-pyrrolidin-1-yl)-benzoic acid

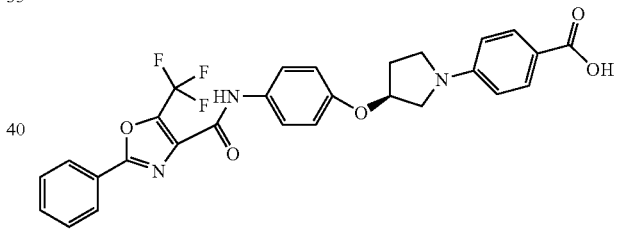

To a mixture of 2-phenyl-5-trifluoromethyl-oxazole-4-carboxylic acid [4-((S)-pyrrolidin-3-yloxy)-phenyl]-amide hydrochloride (180 mg, 0.37 mmol), 4-bromobenzoic acid tert-butyl ester (114 mg, 0.44 mmol), sodium tert-butoxide (118 mg, 1.23 mmol) and (2',4',6'-triisopropyl-1,1'-biphenyl-2-yl)dicyclohexylphosphine (X-PHOS, 40 mg) in dioxane (5 mL) bubbled with argon was added tris(dibenzylideneacetone)dipalladium $Pd_2(dba)_3$ (24 mg). The mixture was heated at 105° C. for 2 hrs. Solvents were evaporated and the residue was extracted with ethyl acetate and 0.1N hydrochloric acid. The organic layer was dried and concentrated. The residue was purified through ISCO column chromatography (silica gel, ethyl acetate in hexane, 5% to 60% linear gradient) to give a white solid as 4-((S)-3-{4-[(2-phenyl-5-trifluoromethyl-oxazole-4-carbonyl)-amino]-phenoxy}-pyrrolidin-1-yl)-benzoic acid tert-butyl ester (150 mg, yield 69%).

The above 4-((S)-3-{4-[(2-phenyl-5-trifluoromethyl-oxazole-4-carbonyl)-amino]-phenoxy}-pyrrolidin-1-yl)-benzoic acid tert-butyl ester (150 mg) was dissolved in a mixture of methylene chloride (2 mL) and trifluoroacetic acid (4 mL). The mixture was stirred at room temperature for 1 hr and solvents were evaporated. The residue was extracted with ethyl acetate and water. The organic layer was dried and solvents were evaporated. The residue was triturated with ethyl acetate and hexanes to give a tan solid as 4-((S)-3-{4-[(2-phenyl-5-trifluoromethyl-oxazole-4-carbonyl)-amino]-phenoxy}-pyrrolidin-1-yl)-benzoic acid (75 mg). LC-MS for $C_{28}H_{22}F_3N_3O_5$ (m/e) calcd 537, obsd 538 (M+H). $^1$H-NMR is consistent with the desired structure.

Example 31

Preparation of 4-(4-{4-[(2-phenyl-5-trifluoromethyl-oxazole-4-carbonyl)-amino]-phenyl}-piperidin-1-yl)-benzoic acid

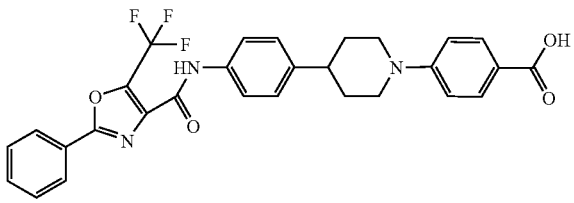

To a mixture of 2-phenyl-5-trifluoromethyl-oxazole-4-carboxylic acid (4-piperidin-4-yl-phenyl)-amide (227 mg, 0.55 mmol), 4-bromobenzoic acid tert-butyl ester (170 mg, 0.66 mmol), sodium tert-butoxide (106 mg, 1.1 mmol) and (2',4',6'-triisopropyl-1,1'-biphenyl-2-yl)dicyclohexylphosphine (X-PHOS, 38 mg) in dioxane (5 mL) bubbled with argon was added tris(dibenzylideneacetone)dipalladium $Pd_2(dba)_3$ (23 mg). The mixture was heated at 105° C. for 2 hrs. Solvents were evaporated and the residue was extracted with ethyl acetate and 0.1N hydrochloric acid. The organic layer was dried and concentrated. The residue was crystallized from ethyl acetate to give a pale yellow solid as 4-(4-{4-[(2-phenyl-5-trifluoromethyl-oxazole-4-carbonyl)-amino]-phenyl}-piperidin-1-yl)-benzoic acid tert-butyl ester (40 mg).

The above 4-(4-{4-[(2-phenyl-5-trifluoromethyl-oxazole-4-carbonyl)-amino]-phenyl}-piperidin-1-yl)-benzoic acid tert-butyl ester (40 mg) was dissolved in a mixture of methylene chloride (2 mL) and trifluoroacetic acid (2 mL). The mixture was stirred at room temperature for 1 hr and solvents were evaporated. The residue was extracted with ethyl acetate and water. The organic layer was dried and solvents were evaporated. The residue was triturated with ethyl acetate to give a solid as 4-(4-{4-[(2-phenyl-5-trifluoromethyl-oxazole-4-carbonyl)-amino]-phenyl}-piperidin-1-yl)-benzoic acid (25 mg). LC-MS for $C_{29}H_{24}F_3N_3O_4$ (m/e) calcd 535, obsd 536 (M+H). $^1$H-NMR is consistent with the desired structure.

Example 32

Preparation of 3-(4-{4-[(2-phenyl-5-trifluoromethyl-oxazole-4-carbonyl)-amino]-phenyl}-piperidin-1-yl)-benzoic acid

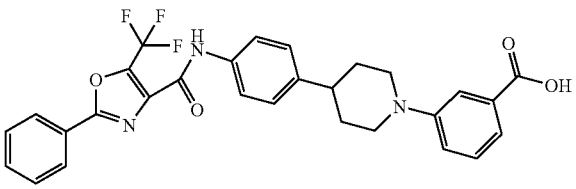

With the same method used for the preparation of 4-(4-{4-[(2-phenyl-5-trifluoromethyl-oxazole-4-carbonyl)-amino]-phenyl}-piperidin-1-yl)-benzoic acid, 3-(4-{4-[(2-phenyl-5-trifluoromethyl-oxazole-4-carbonyl)-amino]-phenyl}-piperidin-1-yl)-benzoic acid was prepared from 2-phenyl-5-trifluoromethyl-oxazole-4-carboxylic acid (4-piperidin-4-yl-phenyl)-amide and 3-bromobenzoic acid tert-butyl ester. LC-MS for $C_{29}H_{24}F_3N_3O_4$ (m/e) calcd 535, obsd 536 (M+H). $^1$H-NMR is consistent with the desired structure.

Example 33

Preparation of 4-(4-{4-[(5-ethyl-2-phenyl-oxazole-4-carbonyl)-amino]-phenyl}-piperidin-1-yl)-benzoic acid

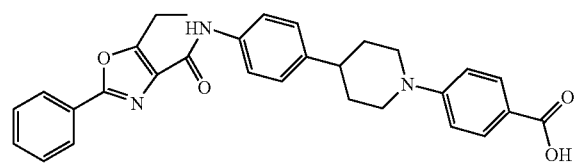

With the same method used for the preparation of 4-(4-{4-[(2-phenyl-5-trifluoromethyl-oxazole-4-carbonyl)-amino]-phenyl}-piperidin-1-yl)-benzoic acid, 3-(4-{4-[(2-phenyl-5-trifluoromethyl-oxazole-4-carbonyl)-amino]-phenyl}-piperidin-1-yl)-benzoic acid was prepared from 2-phenyl-5-ethyl-oxazole-4-carboxylic acid (4-piperidin-4-yl-phenyl)-amide and 4-bromobenzoic acid tert-butyl ester. LC-MS for $C_{30}H_{29}N_3O_4$ (m/e) calcd 495, obsd 496 (M+H). $^1$H-NMR is consistent with the desired structure.

Example 34

DGAT Phospholipid FlashPlate Assay

Materials for the assay are: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (palmitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/ml.

Aqueous buffers and prepared or purchased as follows: The coating buffer (CB) is purchased from PerkinElmer, catalog number SMP900A; the reaction buffer (RB) is 50 mM Tris-HCl, pH 7.5, 100 mM NaCl, 0.01% BSA in water; the washing buffer (WB) is 50 mM Tris-HCl, pH 7.5, 100 mM NaCl, 0.05% deoxycholic acid sodium salt in water; the dilution buffer (DB) is 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 μM with coating buffer (CB). The diluted DAG solution was then added to 384-well PL-FlashPlates at 60 μl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 μM in 100% DMSO. Diluted compound were further diluted 10 fold with reaction buffer (RB). $^{14}$C-Pal-CoA was diluted to 8.3 μM with RB. The DGAT pellet was diluted to 0.13 mg protein/ml with dilution buffer (DB) immediately before it was added to the PL-FlashPlates to start the reaction. 20 μl of the RB-diluted compounds (or 10% DMSO in RB for Total and Blank), 15 μl of RB diluted 14C-Pal-CoA and 15 μl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of IC$_{50}$: The IC$_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. AU data were fitted into a Dose Response One Site model (4 parameter logistic model) as the following:

$$(A+((B-A)/(1+((x/C)^{\wedge}D))))$$

while A and B as the bottom and top of the curve (highest and lowest inhibition), respectively, and C as $IC_{50}$ and D as Hill Coefficient of the compound. The results are summarized in Table 1.

TABLE 1

| Compound | Activity in DGAT Phospholipid FlashPlate Assay (uM) |
|---|---|
| Example 1 | 0.164 |
| Example 2 | 0.280 |
| Example 3 | 0.142 |
| Example 4 | 0.036 |
| Example 5 | 0.212 |
| Example 6 | 0.109 |
| Example 7 | 0.287 |
| Example 8 | 0.309 |
| Example 9 | 0.500 |
| Example 10 | 0.430 |
| Example 11 | 0.185 |
| Example 12 | 0.093 |
| Example 13 | 0.151 |
| Example 14 | 0.167 |
| Example 15 | 0.304 |
| Example 16 | 0.110 |
| Example 17 | 0.066 |
| Example 18 | 0.106 |
| Example 19 | 0.282 |
| Example 20 | 0.106 |
| Example 21 | 0.145 |
| Example 22 | 0.057 |
| Example 23 | 0.051 |
| Example 24 | 0.047 |
| Example 25 | 0.315 |
| Example 26 | 0.215 |
| Example 27 | 0.161 |
| Example 28 | 0.045 |
| Example 29 | 0.142 |
| Example 30 | 0.100 |
| Example 31 | 0.112 |
| Example 32 | 0.118 |
| Example 33 | 0.126 |

It is to be understood that the invention is not limited to the particular embodiments of the invention described above, as variations of the particular embodiments may be made and still fall within the scope of the appended claims.

What is claimed is:
1. A compound of formula (I):

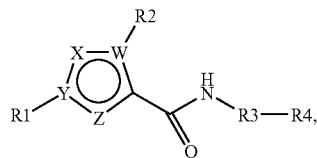

wherein:
X is C, O or N;
Y is C or N;
Z is C or N;
W is C or S, wherein if W is S, then R2 is absent;
R1 is unsubstituted heteroaryl, unsubstituted aryl, or aryl substituted with —OCF3;
R2 is H, lower alkyl or haloloweralkyl;
R3 is phenyl, pyridine or pyrimidine; and
R4 is -piperidine-trifluoromethylphenyl,
-piperazine-1-yl-benzoic acid lower alkyl ester,
-piperazine-pyrimidine,
-piperazine-lower alkoxy phenyl,
-piperazine-trifluoromethylphenyl,
-hydroxy-piperidine-lower alkoxy phenyl,
-piperazine-phenyl,
-hydroxy-piperidine-phenyl,
-piperidine-phenyl,
-hydroxy piperidine-trifluoromethylphenyl,
-piperidine-trifluoromethylphenyl,
-piperazine-halo phenyl,
-piperazine-benzoic acid,
-piperidine-lower alkyl oxadiazole,
-piperidine-cycloloweralkyloxadiazole,
-pyrrolidine-lower alkyl oxadiazole,
-piperidine-pyridinecarboxylic acid,
—O-pyrrolidine-benzoic acid,
—O-pyrrolidine-benzoic acid lower alkyl ester,
-pyrrolidine-benzoic acid lower alkyl ester,
-pyrrolidine-benzoic acid,
-piperidine-benzoic acid, or
-piperidine-benzoic acid lower alkyl ester;
or a pharmaceutically acceptable salt thereof.

2. The compound according to claim 1, wherein X is O and Z is N.

3. The compound according to claim 1, wherein X is N and Y is N.

4. The compound according to claim 1, wherein W is C.

5. The compound according to claim 1, wherein W is C, X is O, Y is C and Z is N.

6. The compound according to claim 1, wherein R1 is phenyl, trifluoromethoxy-phenyl or pyridine.

7. The compound according to claim 1, wherein R2 is methyl, ethyl, trifluoromethyl or hydrogen.

8. The compound according to claim 1, wherein R3 is pyridine or phenyl.

9. The compound according to claim 1, wherein said compound is:
2-phenyl-5-trifluoromethyl-oxazole-4-carboxylic acid [4-(3-trifluoromethyl-phenyl)-3,4,5,6-tetrahydro-2H-[1,2']bipyridinyl-5'-yl]-amide
4-(4-{5-[(2-phenyl-5-trifluoromethyl-oxazole-4-carbonyl)-amino]-pyridin-2-yl}-piperazin-1-yl)-benzoic acid ethyl ester,
2-phenyl-5-trifluoromethyl-oxazole-4-carboxylic acid [6-(4-pyrimidin-2-yl-piperazin-1-yl)-pyridin-3-yl]-amide,
4-(4-{5-[(1-pyridin-2-yl-3-trifluoromethyl-1H-pyrazole-4-carbonyl)-amino]-pyridin-2-yl}-piperazin-1-yl)-benzoic acid ethyl ester,
2-phenyl-5-trifluoromethyl-oxazole-4-carboxylic acid {6-[4-(4-trifluoromethyl-phenyl)-piperazin-1-yl]-pyridin-3-yl}-amide,
2-phenyl-5-trifluoromethyl-oxazole-4-carboxylic acid {6-[4-(4-methoxy-phenyl)-piperazin-1-yl]-pyridin-3-yl}-amide,
2-phenyl-5-trifluoromethyl-oxazole-4-carboxylic acid {6-[4-(2-trifluoromethyl-phenyl)-piperazin-1-yl]-pyridin-3-yl}-amide,
2-phenyl-5-trifluoromethyl-oxazole-4-carboxylic acid {6-[4-(3-trifluoromethyl-phenyl)-piperazin-1-yl]-pyridin-3-yl}-amide, 2-phenyl-5-trifluoromethyl-oxazole-4-carboxylic acid {6-[4-(2-methoxy-phenyl)-piperazin-1-yl]-pyridin-3-yl}-amide,
2-phenyl-5-trifluoromethyl-oxazole-4-carboxylic acid {6-[4-(3-methoxy-phenyl)-piperazin-1-yl]-pyridin-3-yl}-amide,
2-phenyl-5-trifluoromethyl-oxazole-4-carboxylic acid [4-hydroxy-4-(3-trifluoromethyl-phenyl)-3,4,5,6-tetrahydro-2H-[1,2']bipyridinyl-5'-yl]-amide,
2-phenyl-5-trifluoromethyl-oxazole-4-carboxylic acid [6-(4-phenyl-piperazin-1-yl)-pyridin-3-yl]-amide,
2-phenyl-5-trifluoromethyl-oxazole-4-carboxylic acid (4-phenyl-3,4,5,6-tetrahydro-2H-[1,2']bipyridinyl-5'-yl)-amide,
2-phenyl-5-trifluoromethyl-oxazole-4-carboxylic acid (4-hydroxy-4-phenyl-3,4,5,6-tetrahydro-2H-[1,2']bipyridinyl-5'-yl)-amide,
1-pyridin-2-yl-3-trifluoromethyl-1H-pyrazole-4-carboxylic acid [4-(3-trifluoromethyl-phenyl)-3,4,5,6-tetrahydro-2H-[1,2']bipyridinyl-5'-yl]-amide,
1-pyridin-2-yl-3-trifluoromethyl-1H-pyrazole-4-carboxylic acid {6-[4-(4-[4-(fluoro-phenyl)-piperazin-1-yl]-pyridin-3-yl}-amide,
4-(4-{5-[(2-phenyl-5-trifluoromethyl-oxazole-4-carbonyl)-amino]-pyridin-2-yl}-piperazin-1-yl)-benzoic acid,
3-(4-{5-[(2-phenyl-5-trifluoromethyl-oxazole-4-carbonyl)-amino]-pyridin-2-yl}-piperazin-1-yl)-benzoic acid,
2-(4-5-[(2-phenyl-5-trifluoromethyl-oxazole-4-carbonyl)-amino]-pyridin-2-yl}-piperazin-1-yl)-benzoic acid,
2-phenyl-5-trifluoromethyl-oxazole-4-carboxylic acid {4-[4-(3-isopropyl-[1,2,4]oxadiazol-5-yl)-piperidin-1-yl]-phenyl}-amide,
2-phenyl-5-trifluoromethyl-oxazole-4-carboxylic acid [2-[4-(3-isopropyl-[1,2,4]oxadiazol-5-yl)-piperidin-1-yl]-pyrimidin-5-yl]-amide;
2-phenyl-5-trifluoromethyl-oxazole-4-carboxylic acid [4-(3-isopropyl-[1,2,4]oxadiazol-5-yl)-3,4,5,6-tetrahydro-2H-[1,2']bipyridinyl-5'-yl]-amide,
2-phenyl-5-trifluoromethyl-oxazole-4-carboxylic acid [4-(3-methyl-[1,2,4]oxadiazol-5-yl)-3,4,5,6-tetrahydro-2H-[1,2']bipyridinyl-5'-yl]-amide,
2-phenyl-5-trifluoromethyl-oxazole-4-carboxylic acid [4-(3-cyclopropyl-[1,2,4]oxadiazol-5-yl)-3,4,5,6-tetrahydro-2H-[1,2']bipyridinyl-5'-yl]-amide,
2-phenyl-5-trifluoromethyl-oxazole-4-carboxylic acid {6-[3-(3-isopropyl-[1,2,4]oxadiazol-5-yl)-pyrrolidin-1-yl]-pyridin-3-yl}-amide,
2-(2-trifluoromethoxy-phenyl)-5-trifluoromethyl-oxazole-4-carboxylic acid [4-(3-isopropyl-[1,2,4]oxadiazol-5-yl)-3,4,5,6-tetrahydro-2H-[1,2']bipyridinyl-5'-yl]-amide,
4-{4-[(2-phenyl-5-trifluoromethyl-oxazole-4-carbonyl)-amino]-phenyl}-3,4,5,6-tetrahydro-2H-[1,2']bipyridinyl-5'-carboxylic acid,
4-{4-[(4-phenyl-thiophene-2-carbonyl)-amino]-phenyl}-3,4,5,6-tetrahydro-2H-[1,2']bipyridinyl-5'-carboxylic acid,
4-{4-[(5-methyl-2-phenyl-oxazole-4-carbonyl)-amino]-phenyl}-3,4,5,6-tetrahydro-2H-[1,2']bipyridinyl-5'-carboxylic acid,
4-((S)-3-{4-[(2-phenyl-5-trifluoromethyl-oxazole-4-carbonyl)-amino]-phenoxy}-pyrrolidin-1-yl)-benzoic acid,
4-(4-{4-[(2-phenyl-5 trifluoromethyl-oxazole-4-carbonyl)-amino]-phenyl}-piperidin-1-yl)-benzoic acid,
3-(4-{4-[(2-phenyl-5-trifluoromethyl-oxazole-4-carbonyl)-amino]-phenyl}-piperidin-1-yl)-benzoic acid, or
4-(4-{4-[(5-ethyl-2-phenyl-oxazole-4-carbonyl)-amino]-phenyl}-piperidin-1-yl)-benzoic acid.

10. The compound of claim 1 wherein said compound is of the formula:

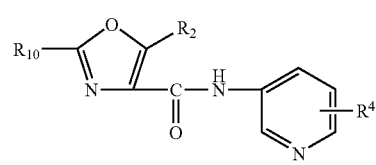

wherein $R_{10}$ is heteroaryl, phenyl, or phenyl substituted with —$OCF_3$; or its pharmaceutically acceptable salts.

11. The compound of claim 10 wherein R4 is piperidine-trifluoromethylphenyl, hydroxy-piperidine-lower alkoxy phenyl, hydroxy-piperidine-phenyl, piperidine-trifluoromethylphenyl, piperidine-lower alkyl oxadiazole, piperidine-pyridinecarboxylic acid, piperidine-cyclopropyloxadiazole, piperidine-benzoic acid, piperidine-benzoic acid lower alkyl ester, piperidine-phenyl, or hydroxy piperidine-trifluoromethylphenyl.

12. The compound of claim 11 wherein said compound is 2-phenyl-5-trifluoromethyl-oxazole-4-carboxylic acid [4-(3-trifluoromethyl-phenyl)-3,4,5,6-tetrahydro-2H-[1,2']bipyridinyl-5'-yl]-amide or its pharmaceutically acceptable salts.

13. The compound of claim 11 wherein said compound is 2-phenyl-5-trifluoromethyl-oxazole-4-carboxylic acid [4-hydroxy-4-(3-trifluoromethyl-phenyl)-3,4,5,6-tetrahydro-2H-[1,2']bipyridinyl-5'-yl]-amide or its pharmaceutically acceptable salts.

14. The compound of claim 11 wherein said compound is 2-phenyl-5-trifluoromethyl-oxazole-4-carboxylic acid (4-phenyl-3,4,5,6-tetrahydro-2H-[1,2']bipyridinyl-5'-yl)-amide or its pharmaceutically acceptable salts.

15. The compound of claim 11 wherein said compound is 2-phenyl-5-trifluoromethyl-oxazole-4-carboxylic acid (4-hydroxy-4-phenyl-3,4,5,6-tetrahydro-2H-[1,2']bipyridinyl-5'-yl)-amide or its pharmaceutically acceptable salts.

16. The compound of claim 10 wherein R4 is piperidine-lower alkyl oxadiazole or piperidine-cycloloweralkyloxadiazole.

17. The compound of claim 16 wherein said compound is 2-phenyl-5-trifluoromethyl-oxazole-4-carboxylic acid [4-(3-isopropyl-[1,2,4]oxadiazol-5-yl)-3,4,5,6-tetrahydro-2H-[1,2']bipyridinyl-5'-yl]-amide or its pharmaceutically acceptable salts.

18. The compound of claim 16 wherein said compound is 2-phenyl-5-trifluoromethyl-oxazole-4-carboxylic acid [4-(3-methyl-[1,2,4]oxadiazol-5-yl)-3,4,5,6-tetrahydro-2H-[1,2'] bipyridinyl-5'-yl]-amide or its pharmaceutically acceptable salts.

19. The compound of claim 16 wherein said compound is 2-phenyl-5-trifluoromethyl-oxazole-4-carboxylic acid [4-(3-cyclopropyl-[1,2,4]oxadiazol-5-yl)-3,4,5,6-tetrahydro-2H-[1,2']bipyridinyl-5'-yl]-amide or its pharmaceutically acceptable salts.

20. The compound of claim 16 wherein said compound is 2-(2-trifluoromethoxy-phenyl)-5-trifluoromethyl-oxazole-4-carboxylic acid [4-(3-isopropyl-[1,2,4]oxadiazol-5-yl)-3, 4,5,6-tetrahydro-2H-[1,2']bipyridinyl-5'-yl]-amide or its pharmaceutically acceptable salts.

21. The compound of claim 10 wherein R4 is piperazine-1-yl-benzoic acid lower alkyl ester, -piperazine-phenyl, piperazine-halo phenyl, piperazine-benzoic acid, piperazine-pyrimidine, piperazine-lower alkoxy phenyl or piperazine-trifluoromethylphenyl.

22. The compound of claim 21 wherein said compound is 4-(4-{5-[(2-phenyl-5-trifluoromethyl-oxazole-4-carbonyl)-amino]-pyridin-2-yl}-piperazin-1-yl)-benzoic acid ethyl ester or its pharmaceutically acceptable salts.

23. The compound of claim 21 wherein said compound is 2-phenyl-5-trifluoromethyl-oxazole-4-carboxylic acid [6-(4-pyrimidin-2-yl-piperazin-1-yl)-pyridin-3-yl]amide or its pharmaceutically acceptable salts.

24. The compound of claim 21 wherein said compound is 2-phenyl-5-trifluoromethyl-oxazole-4-carboxylic acid {6-[4-(3-methoxy-phenyl)-piperazin-1-yl]-pyridin-3-yl}-amide or its pharmaceutically acceptable salts.

25. The compound of claim 21 wherein said compound is 2-phenyl-5-trifluoromethyl-oxazole-4-carboxylic acid {6-[4-(4-trifluoromethyl-phenyl)-piperazin-1-yl]-pyridin-3yl}-amide or its pharmaceutically acceptable salts.

26. The compound of claim 21 wherein said compound is 2-phenyl-5-trifluoromethyl-oxazole-4-carboxylic acid {6-[4-(4-methoxy-phenyl)-piperazin-1-yl]-pyridin-3-yl}-amide or its pharmaceutically acceptable salts.

27. The compound of claim 21 wherein said compound is 2-phenyl-5-trifluoromethyl-oxazole-4-carboxylic acid {6-[4-(2-trifluoromethyl-phenyl)-piperazin-1-yl]-pyridin-3-yl}-amide or its pharmaceutically acceptable salts.

28. The compound of claim 21 wherein said compound is 2-phenyl-5-trifluoromethyl-oxazole-4-carboxylic acid {6-{4-(3-trifluoromethyl-phenyl)-piperazin-1-yl]-pyridin-3-yl}-amide or its pharmaceutically acceptable salts.

29. The compound of claim 21 wherein said compound is 2-phenyl-5-trifluoromethyl-oxazole-4-carboxylic acid {6-[4-(2-methoxy-phenyl)-piperazin-1-yl]-kpyridin-3-yl}-amide or its pharmaceutically acceptable salts.

30. The compound of claim 21 wherein said compound is 2-phenyl-5-trifluoromethyl-oxazole-4-carboxylic acid [6-(4-phenyl-piperazin-1-yl)-pyridin-3-yl]-amide or its pharmaceutically acceptable salts.

31. The compound of claim 21 wherein said compound is 4-(4-{5-[(2-phenyl-5-trifluoromethyl-oxazole-4-carbonyl)-amino]-pyridin-2-yl)-piperazin-1-yl)-benzoic acid or its pharmaceutically acceptable salts.

32. The compound of claim 21 wherein said compound is 3-(4-{5-[(2-phenyl-5-trifluoromethyl-oxazole-4-carbonyl)-amino]-pyridin-2-yl}-piperazin-1-yl)-benzoic acid or its pharmaceutically acceptable salts.

33. The compound of claim 21 wherein said compound is 2-(4-{5-[(2-phenyl-5-trifluoromethyl-oxazole-4-carbonyl)-amino}-pyridin-2-yl}-piperazin-1-yl)-benzoic acid or its pharmaceutically acceptable salts.

34. The compound of claim 10 wherein R4 is pyrrolidine-lower alkyl oxadiazole, or O-pyrrolidine-benzoic acid or O-pyrrolidine-benzoic acid lower alkyl ester.

35. The compound of claim 34 wherein said compound is 2-phenyl-5-trifluoromethyl-oxazole-4-carboxylic acid {6-[3-(3-isopropyl-[1,2,4]oxadiazol-5-yl)-pyrrolidin-1-yl]-pyridin-3-yl}-amide or its pharmaceutically acceptable salts.

36. The compound of claim 1 wherein said compound is

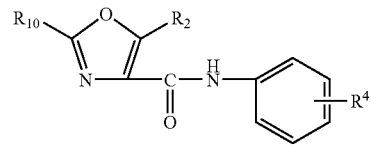

wherein $R_{10}$ is heteroaryl, phenyl, or phenyl substituted with —$OCF_3$; or its pharmaceutically acceptable salts.

37. The compound of claim 36 wherein R4 is piperidine-trifluoromethylphenyl, hydroxy-piperidine-lower alkoxy phenyl, hydroxy-piperidine-phenyl, piperidine-trifluoromethylphenyl, piperidine-lower alkyl oxadiazole, piperidine-pyridinecarboxylic acid, piperidine-cycloloweralkyloxadiazole, piperidine-benzoic acid, piperidine-benzoic acid lower alkyl ester, piperidine-phenyl, or hydroxy piperidine-trifluoromethylphenyl.

38. The compound of claim 36 wherein said compound is 4-{4-{(5-methyl-2-phenyl-oxazole-4-carbonyl)-aminol-phenyl}-3,4,5,6-tetrahydro-2H-[1,2']bipyridinyl-5'-carboxylic acid or its pharmaceutically acceptable salts.

39. The compound of claim 37 wherein said compound is 4-(4-{4-[(2-phenyl-5-trifluoromethyl-oxazole-4-carbonyl)-amino]-phenyl}-piperidin-1-yl)-benzoic acid or its pharmaceutically acceptable salts.

40. The compound of claim 37 wherein said compound is 3-(4-{4-[(2-phenyl-5-trifluoromethyl-oxazole-4-carbonyl)-amino]-phenyl}-piperidin-1-yl)-benzoic acid or its pharmaceutically acceptable salts.

41. The compound of claim 37 wherein said compound is 4-(4-{4-[(5-ethyl-2-phenyl-oxazole-4-carbonyl)-amino]-phenyl}-piperidin-1-yl)-benzoic acid or its pharmaceutically acceptable salts.

42. The compound of claim 36 wherein R4 is pyrrolidine-lower alkyl oxadiazole, O-pyrrolidine-benzoic acid or O-pyrrolidine-benzoic acid lower alkyl ester.

43. The compound of claim 42 wherein said compound is 4-(3-{4-[(2-phenyl-5-trifluoromethyl-oxazole-4-carbonyl)-amino]-phenoxy}-pyrrolidin-1-yl)-benzoic acid or its pharmaceutically acceptable salts.

44. The compound of claim 36 wherein R4 is piperidine-lower alkyl oxadiazole or piperidine-cycloloweralkyloxadiazole.

45. The compound of claim 44 wherein said compound is 2-phenyl-5-trifluoromethyl-oxazole-4-carboxylic acid {4-[4-(3-isopropyl-[1,2,4]oxadiazol-5-yl)-piperidin-1-yl]-phenyl}-amide or its pharmaceutically acceptable salts.

46. The compound of claim 1 wherein said compound is of the formula:

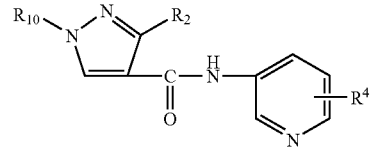

wherein $R_{10}$ is heteroaryl, phenyl or phenyl substituted with —$OCF_3$; or its pharmaceutically acceptable salts.

47. The compound of claim 46 wherein $R_{10}$ is a heteroaryl contains a 5 or 6 membered ring with from 1 to 2 heteroatoms selected from the group consisting of N, O and S.

48. The compound of claim 47 wherein R4 is piperazine-1-yl-benzoic acid lower alkyl ester, -piperazine-phenyl, piperazine-halophenyl, piperazine-benzoic acid, piperazine-pyrimidine, piperazine-lower alkoxy phenyl, or piperazine-trifluoromethylphenyl.

49. The compound of claim 47 wherein said compound is 4-(4-{5-[(1-pyridin-2-yl-3-trifluoromethyl-1H-pyrazole-4-carbonyl)-amino]-pyridin-2-yl}-piperazin-1-yl)-benzoic acid ethyl ester or its pharmaceutically acceptable salts.

50. The compound of claim 47 wherein said compound is 1-pyridin-2-yl-3-trifluoromethyl-1H-pyrazole-4-carboxylic acid {6-[4-(4-fluoro-phenyl)-piperazin-1-yl]-pyridin-3-yl}-amide or its pharmaceutically acceptable salts.

51. The compound of claim 46 wherein R4 is piperidine-trifluoromethylphenyl, hydroxy-piperidine-lower alkoxy phenyl, hydroxy-piperidine-phenyl, piperidine-trifluoromethylphenyl, piperidine-lower alkyl oxadiazole, piperidine-lower alkyl oxadiazole, piperidine-pyridinecarboxylic acid, piperidine-cyclopropyloxadiazole, piperidine-benzoic acid, piperidine-phenyl, or hydroxy piperidine-trifluoromethylphenyl.

52. The compound of claim 47 wherein said compound is 1-pyridin-2-yl-3-trifluoromethyl-1H-pyrazole-4-carboxylic acid [4-(3-trifluoromethyl-phenyl)-3,4,5,6-tetrahydro-2H-[1,2']bipyridinyl-5'-yl]-amide or its pharmaceutically acceptable salts.

53. The compound of claim 1 wherein said compound is of the formula:

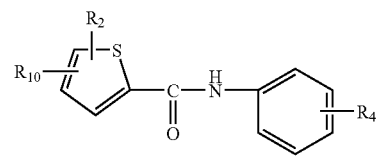

wherein $R_{10}$ is heteroaryl, phenyl or phenyl substituted with an —$OCF_3$; or its pharmaceutically acceptable salts.

54. The compound of claim 53 wherein R4 is piperidine-trifluoromethylphenyl, hydroxy-piperidine-lower alkoxy phenyl, hydroxy-piperidine-phenyl, piperidine-trifluoromethylphenyl, piperidine-lower alkyl oxadiazole, piperidine-pyridinecarboxylic acid, piperidine-cycloloweralkyloxadiazole, piperidine-benzoic acid, piperidine-phenyl, piperidine-benzoic acid lower alkyl ester or hydroxy piperidine-trifluoromethylphenyl.

55. The compound of claim 53 wherein said compound is 4-{4-[(4-phenyl-thiophene-2-carbonyl)-amino]-phenyl}-3,4,5,6-tetrahydro-2H-[1,2']bipyridinyl-5'-carboxylic acid or its pharmaceutically acceptable salts.

\* \* \* \* \*

UNITED STATES PATENT AND TRADEMARK OFFICE
CERTIFICATE OF CORRECTION

| | | |
|---|---|---|
| PATENT NO. | : 8,211,914 B2 | Page 1 of 1 |
| APPLICATION NO. | : 12/638244 | |
| DATED | : July 3, 2012 | |
| INVENTOR(S) | : David R. Bolin et al. | |

It is certified that error appears in the above-identified patent and that said Letters Patent is hereby corrected as shown below:

Claim 10, at column 58, lines 10 to 17, that portion reading "$R_2$" should read --R2--; that portion reading "$R_4$" should read --R4--.

Claim 29, at column 59, line 41, that portion reading "kpyridin-3-yl" should read --pyridin-3-yl--.

Claim 36, at column 60, lines 2 to 9, that portion reading "$R_2$" should read --R2--; that portion reading "$R_4$" should read --R4--.

Claim 46, at column 60, lines 55 to 61, that portion reading "$R_2$" should read --R2--; that portion reading "$R_4$" should read --R4--.

Claim 51, at column 61, lines 16 to 17, cancel the duplicate phrase "piperidine-lower alkyl oxadiazole".

Claim 53, at column 62, lines 1 to 8, the formula should appear as follows:

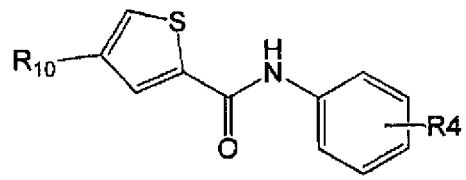

Signed and Sealed this
First Day of January, 2013

David J. Kappos
*Director of the United States Patent and Trademark Office*